(12) United States Patent
Kastner et al.

(10) Patent No.: US 10,138,306 B1
(45) Date of Patent: Nov. 27, 2018

(54) METHACRYLIC ACID PRODUCTION METHOD

(71) Applicant: University of Georgia Research Foundation, Inc., Athens, GA (US)

(72) Inventors: James Kastner, Athens, GA (US); Maryam Pirmoradi, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/390,069

(22) Filed: Dec. 23, 2016

Related U.S. Application Data

(60) Provisional application No. 62/247,545, filed on Oct. 28, 2015.

(51) Int. Cl.
*C07C 51/00* (2006.01)
*C08F 20/06* (2006.01)
*B01J 23/44* (2006.01)
*B01J 21/10* (2006.01)
*C07C 51/38* (2006.01)
*B01J 23/46* (2006.01)
*C08F 20/14* (2006.01)

(52) U.S. Cl.
CPC .............. *C08F 20/06* (2013.01); *B01J 21/10* (2013.01); *B01J 23/44* (2013.01); *B01J 23/464* (2013.01); *C07C 51/38* (2013.01); *C08F 20/14* (2013.01)

(58) Field of Classification Search
None
See application file for complete search history.

(56) References Cited

U.S. PATENT DOCUMENTS

2014/0213811 A1   7/2014   Dubois et al.

FOREIGN PATENT DOCUMENTS

WO    WO 2014002886 A1 *   1/2013
WO    2016001033           1/2016

OTHER PUBLICATIONS

Tmachine ranslation for WO 2014002886 A1.*
Ai M., Fujihashi H., Hosoi S., Yoshida A. (2003) Production of methacrylic acid by vapor-phase aldol condensation of propionic acid with formaldehyde over silica-supported metal phosphate catalysts. Applied catalysis A: general 252:185-191.
Albers P., Pietsch J., Parker S.F.(2001) Poisoning and deactivation of palladium catalysts. Journal of Molecular catalysis A: Chemical 173:275-286.
An J., Bagnell L., Cablewski T., Strauss C.R., Trainor R.W. (1997) Applications of high-temperature aqueous media for synthetic organic reactions. The Journal of organic chemistry 62:2505-2511.
Beck D.D., Sommers J.W. (1995) Impact of sulfur on the performance of vehicle-aged palladium monoliths. Applied catalysis B: Environmental 6:185-200.
Carlsson M., Habenicht C., Kam L.C., Antal M.J.J., Bian N., Cunningham R.J., Jones M.J. (1994) Study of the sequential conversion of citric to itaconic to methacrylic acid in near-critical and supercritical water. Industrial & engineering chemistry research 33:1989-1996.
Fu J., Shi E, Thompson Jr L., Lu X., Savage P.E. (2011) Activated carbons for hydrothermal decarboxylation of fatty acids. ACS Catalysis 1:227-231.
Hattori H. (2014) Solid base catalysts: fundamentals and their applications in organic reactions. Applied Catalysis A: General.
Kuenz A., Gallenmüller Y., Willke T., Vorlop K.-D. (2012) Microbial production of itaconic acid: developing a stable platform for high product concentrations. Applied microbiology and biotechnology 96:1209-1216.
Kus N.S. (2012) Organic reactions in subcritical and supercritical water. Tetrahedron 68:949-958.
L'Argentière P., Liprandi D., Cagnola E., Fígoli N. (1997) [PdCl2 (NH2(CH2)12CH3)2] supported on γ-Al2O3 as catalyst for selective hydrogenation. Catalysis letters 44:101-107.
Le Nôtre J., Witte-van Dijk S., van Haveren J., Scott E.L., Sanders J.P. (2014) Synthesis of Bio-Based Methacrylic Acid by Decarboxylation of Itaconic Acid and Citric Acid Catalyzed by Solid Transition-Metal Catalysts. ChemSusChem 7:2712-2720.
Li J., Brill T.B. (2001) Spectroscopy of Hydrothermal Reactions 16: Kinetics of Decarboxylation/Hydrolysis of Methyl Propiolate Ester and Decarboxylation of Propiolic Acid at 150-210° C. and 275 Bar. The Journal of Physical Chemistry A 105:6171-6175.
Matsubara S., Yokota Y., Oshima K. (2004) Palladium-catalyzed decarboxylation and decarbonylation under hydrothermal conditions: decarboxylative deuteration. Organic letters 6:2071-2073.
Na J.-G., Yi B.E., Kim J.N., Yi K.B., Park S.-Y., Park J.-H., Kim J.-N., Ko C.H. (2010) Hydrocarbon production from decarboxylation of fatty acid without hydrogen. Catalysis Today 156:44-48.
Nikolopoulos A., Jang B.-L., Spivey J. (2005) Acetone condensation and selective hydrogenation to MIBK on Pd and Pt hydrotalcite-derived Mg Al mixed oxide catalysts. Applied Catalysis A: General 296:128-136.
Onda A., Ochi T., Kajiyoshi K., Yanagisawa K. (2008) Lactic acid production from glucose over activated hydrotalcites as solid base catalysts in water. Catalysis Communications 9:1050-1053.
Pyo S.-H., Dishisha T., Dayankac S., Gerelsaikhan J., Lundmark S., Rehnberg N., Hatti-Kaul R. (2012) A new route for the synthesis of methacrylic acid from 2-methyl-1, 3-propanediol by integrating biotransformation and catalytic dehydration. Green Chemistry 14:1942-1948.
Spivey J.J., Gogate M.R., Zoeller J.R., Colberg R.D. (1997) Novel catalysts for the environmentally friendly synthesis of methyl methacrylate. Industrial & engineering chemistry research 36:4600-4608.
Steiger M.G., Blumhoff M.L., Mattanovich D., Sauer M. (2013) Biochemistry of microbial itaconic acid production. Frontiers in microbiology 4.

(Continued)

*Primary Examiner* — Ana Z Muresan
(74) *Attorney, Agent, or Firm* — Thomas|Horstemeyer, LLP

(57) ABSTRACT

A method of producing methacrylic acid using a hydrotalcite catalyst and subcritical water is described.

22 Claims, 12 Drawing Sheets

(56) References Cited

OTHER PUBLICATIONS

Tai J., Davis R.J. (2007) Synthesis of methacrylic acid by aldol condensation of propionic acid with formaldehyde over acid-base bifunctional catalysts. Catalysis today 123:42-49.
White R.J., Luque R., Budarin V.L., Clark J.H., Macquarrie D.J. (2009) Supported metal nanoparticles on porous materials. Methods and applications. Chemical Society Reviews 38:481-494.
Willke T., Vorlop K.-D. (2001) Biotechnological production of itaconic acid. Applied microbiology and biotechnology 56:289-295.
Xu C., Teja A.S. (2006) Supercritical water synthesis and deposition of iron oxide ($\alpha$-Fe2O3) nanoparticles in activated carbon. The Journal of supercritical fluids 39:135-141.

\* cited by examiner

Renewable Sugars to Biobased Methacrylic Acid

PARR 5000 Multiple Reactor System

METHACRYLIC ACID PRODUCTION METHOD

In recent years, continued utilization of fossil resources has raised environmental and economic concerns. Hence, the chemical industry has started stepping towards utilization of bio-renewable and bio-based replacements for fossil-based resources. Bioethanol is a significant example of bio-based chemical production in large scale. One of the most important branches of chemical industry is the production of polymers. One bio-based approach in production of polymers is using monomers that are synthesized from bio-based feedstocks instead of fossil resources. This approach leads to the use of monomers identical to those generated previously from fossil resources which means that the production of polymers and their processing remains the same. 2-methylpropenoic acid, known more familiarly as methacrylic acid (MAA), is an organic acid with one carboxyl group as the main functional group. This organic acid is a significant monomer in the polymer industry, since it is used as a precursor for its esters like methyl methacrylate (MMA) and poly (methyl methacrylate) (PMMA). MAA and MMA also participate in the composition of methyl methacrylate-butadiene-styrene co-polymers or modified polyvinyl chloride. Polymers synthesized from methacrylic acid and methyl methacrylate are chemically resistant and transparent so they can be used as glass substitutes and in optical fibers. MAA and MMA are also used in the preparation of adhesives and paintings.

Industrially, methacrylic acid is produced using the hazardous acetone-cyanohydrin process. In acetone-cyanohydrin process, acetone and hydrogen cyanide are reacted with concentrated sulphuric acid resulting in methacrylamide acid sulphate. Further treatments with methanol, hydrolysis and esterification of amide are necessary to produce a mixture of MMA and MAA. Severe problems such as toxic starting material, high process cost and high amount of bisulfate waste that must be disposed cannot be ignored in acetone-cyanohydrin process. Recently several research groups have reported the synthesis of MAA or MMA from bio-based substrates. The production of MAA by two consecutive steps that involve an oxidative bio-conversion and a catalytic dehydration of 2-methyl-1,3-propanediol, which can be resulted from the fermentation of glycerol, is reported. Fermentation derived isobutyric acid is a known precursor of MAA by catalytic oxidative dehydrogenation.

2-methylenesuccinic acid or itaconic acid is an important chemical that can be obtained from biomass. Itaconic acid is non-toxic and readily biodegradable. Industrially, it is produced by the fermentation of carbohydrates such as glucose using *Aspergillus terreus*. Its current global production is approximately 80000 tons. Itaconic acid can be converted to methacrylic acid by one step decarboxylation. In a bio/catalytic approach, it is reported that methacrylic acid is synthesized from fermentation derived itaconic acid using solid transition-metal catalysts such as Pd/C, Pt/Al$_2$O$_3$, and Ru/C and homogeneous base catalysts such as sodium hydroxide.

It is well understood that application of homogeneous base catalysts in chemical processes causes severe problems such as corrosion of reactors, difficult separation and recycling of the catalyst, high costs of waste disposal and wastewater treatment. In this work, methacrylic acid is synthesized by one-step decarboxylation of itaconic acid using solid-base catalysts such as hydrotalcite. Hydrotalcite is a layered anionic clay with base sites originating from HCO$^-_3$ on the hydrophilic surface. This solid-base catalyst can be employed in decarboxylation processes. Using hydrotalcite in decarboxylation of fatty acids is reported in literature. This work proposes a comprehensive study on the effect of solid-base catalysts on methacrylic acid yield in decarboxylation process of itaconic acid.

Methacrylic acid is used in production of plastic sheets, moldings, fibers, resins and other organic compounds. The major product of methacrylic acid and methyl methacrylate is poly (methyl methacrylate), with an annual consumption of 2.1 million tons (Pyo et al., 2012). Currently, hazardous acetone-cyanohydrin process is the main process in production of methacrylic acid. Severe problems such as toxic starting material, high process cost and high amount of bisulfate waste that must be disposed cannot be ignored in acetone-cyanohydrin process. Another industrial route to methacrylic acid involves two oxidation steps. The first step is oxidation of isobutylene to methacrolein over mixed metal oxides of Mo and Fe, with promoters such as Co, Ni, and an alkali metal (Bauer, 1990). The second step involves oxidation of methacrolein to methacrylic acid that can take place over a phosphomolybidic catalyst containing Cu and V and alkali metal promoters. Other routes to methacrylic acid, based on C$_2$ compounds, have also been studied. The processes based on C$_2$ carbonylation, shown in FIG. 1, are implemented technologies in production of methacrylic acid and methyl methacrylate. Each of the processes, shown in FIG. 1, involves propionate as an intermediate, which is condensed with formaldehyde to produce either methacrylic acid or a mixture of methacrylic acid and methyl methacrylate. In process III, the water produced in the partial oxidation reaction hydrolyzes some propionic acid anhydride to form propionic acid, which is recycled. Synthesis of methacrylic acid by vapor-phase aldol condensation of propionic acid with formaldehyde over silica-supported metal phosphate catalysts (Ai et al., 2003) and acid-base bifunctional catalysts such as MgO, SiO$_2$, Al$_2$O$_3$ and ZrO$_2$, with and without cesium (Tai and Davis, 2007) has also been reported.

In the last two decades, some research groups have reported bio/catalytic approaches in production of methacrylic acid. In 1994, Carlsson et al. studied sequential conversion of fermentation-derived citric acid to itaconic acid to methacrylic acid in near critical (220-370° C.) and super critical water (375-400° C.). Since one hydroxyl and three carboxyl groups are the main functional groups of citric acid, it reacts at high temperatures to make reactive products that can participate in the secondary reactions. Acids with a tertiary hydroxyl in a position can decompose to a ketone in high temperatures (Johnson, 1979). Therefore citric acid decomposes to acetone dicarboxylic acid that further decomposes to acetone at elevated temperatures (Bouchard et al. 1979). β-Hydroxy acids dehydrate to an α-β unsaturated acids (with the loss of carbon dioxide) at high temperatures (Carlsson et al., 1994). Therefore cis/trans-aconitic acid is an unstable intermediate of citric acid. Bruce et al. 1943 reported that aconitic acid decomposes to itaconic acid at temperatures higher than 180° C. Itaconic acid can form methacrylic acid with one decarboxylation step. Propene dicarboxylic acids equilibration in water solutions occurs very fast at high temperatures (Le Nôtre et al., 2014), hence itaconic acid may involve a fast reaction and be in equilibrium with citraconic acid and mesaconic acid; more rapidly than it decarboxylates to methacrylic acid. According to a study by Li et al. 2001 on the kinetics of non-catalyzed reactions under near critical water conditions, the rate of isomerization is faster than decarboxylation and the rate of decarboxylation is faster than hydration. Hence, mesaconic acid and citraconic acid are the results of itaconic acid isomerization. In the next step, itaconic acid and its isomers can decarboxylate to methacrylic acid and crotonic acid. Itaconic acid can also form citramalic acid by adding water across its double bond. FIG. 2 shows the suggested reaction pathways for citric acid decomposition in hot liquid water.

Carlsson et al. 1994 experiments were performed at temperatures ranging from 220 to 400° C. and at pressure of 34.5 MPa in plug flow reactors using sodium hydroxide as a homogeneous base catalyst. They reported that decarboxylation of itaconic acid is fast above 350° C., although formation of byproducts such as acetic acid, pyruvic acid, acetone, and acetaldehyde and also methacrylic acid degradation products such as propene indicate a loss of selectivity at these temperatures. Decarboxylation of citric acid to itaconic acid is relatively slow with high selectivity at 250° C. and below. At all tested temperatures, independent of the substrate (itaconic acid or citric acid), almost identical byproducts were obtained. Results of studying the effect of itaconic acid residence time on methacrylic acid yield verifies that methacrylic acid yield rises rapidly to almost a steady state value. Methacrylic acid is not stable in water at high temperatures. Like itaconic acid, methacrylic acid can also add water across its double bond, forming 2-hydroxy-isobutyric acid. Degradation of 2-hydroxyisobutyric acid leads to the formation of pyruvic acid, acetone and other volatile compounds (Le Nôtre et al., 2014). 2-hydroxyisobutyric acid can also be produced from decarboxylation of citramalic acid. Methacrylic acid may also decarboxylate to form propene which can react with the remaining methacrylic acid and form its propyl ester (Bauer, 1990).

Synthesis of methacrylic acid by decarboxylation of itaconic acid and citric acid catalyzed by solid-transition metal catalysts is also reported (Le Nôtre et al., 2014). Transition metals with typical supports such as Pd/C, Ru/C, Pt/C and Pt/Al$_2$O$_3$ were tested for decarboxylation of itaconic acid and citric acid (in water) to methacrylic acid in batch reactors at temperatures of 200-250° C. and pressure of 1 bar argon. The highest methacrylic acid yields were achieved with Pd/C and Pt/C at 250° C.

In an enzymatic approach, acrylic acid and methacrylic acid are synthesized from enzymatic conversion of acrylonitrile and methacrylonitrile, respectively. ε-Caprolactam-induced *Rhodococcus rhodochrous* J1 cells containing nitrilase are used for production of both acrylic acid and methacrylic acid (Nagasawa et al., 1990). Pyo et al. 2012 also reported production of methacrylic acid by two consecutive steps that involve a bio-oxidation and a catalytic dehydration of 2-methyl-1,3-propanediol. Methacrylic acid is produced by a process involving bio-conversion of 2-methyl-1,3-propanediol to 3-hydroxy-2-methylpropionic acid via 3-hydroxy-2-methyl propanal and catalytic dehydration of the resulting acid. Cells of *Gluconobacter oxydans* grown on glycerol-based culture medium are used as the catalyst for bioconversion that involves alcohol dehydrogenase and aldehyde dehydrogenase enzymes. The product of bio-conversion is converted to methacrylic acid using titanium dioxide at 210° C.

Base catalysts are important in the areas of organic synthesis of fine and intermediate chemicals in particular. In base catalysis, a reaction is usually catalyzed by a hydroxide ion. There are many possible compounds that can act as sources for hydroxide ion such as sodium hydroxide and potassium hydroxide. These sources of hydroxide ion can catalyze the chemical reactions homogeneously (liquid base catalysts). However, application of homogeneous acid and base catalysts in chemical processes causes severe problems such as corrosion of reactors, difficult separation and recycling of the catalyst, high costs of waste disposal and waste water treatment. One effective step towards more environmental friendly processes is replacement of homogeneous catalytic systems by heterogeneous catalytic systems. In solid-base catalysis, basic sites usually appear as Bronsted base (a base accepts a proton from reactant) or Lewis base (a base donates an electron pair to the reactant). An example of Bronsted base catalysis is aldol condensation and Knoevenagel condensation where an $H^+$ is abstracted from ketone with α-H to form anions. The Tishchenko reaction where a basic site donates an electron pair to the carbonyl C atoms to form anions is an example for Lewis base catalysis. Table 1 is a list of different types of solid base catalysts. In solid base catalysts, basic sites appear on the surface. By removing $CO_2$ and $H_2O$ from the surface of base catalysts, Surface O atoms of metal oxides are exposed. To remove $CO_2$ and $H_2O$ and have basic sites on surface, pretreatment at high temperatures is required (Hattori, 2014). The optimum pretreatment temperature depends on the type of reaction and the type of catalyst.

TABLE 1

Types of solid base catalysts (Hattori 2014).

(1) Single component metal oxides
    alkaline earth metal oxides: MgO, CaO, SrO, BaO
    rare earth oxides: $La_2O_3$, $Sm_2O_3$
    other oxides: $Al_2O_3$, $ZrO_2$, $Y_2O_3$, ZnO, $TiO_2$, $MoO_3$, $ThO_2$
(2) Double components metal oxide
    ZnO—$Al_2O_3$, MgO—$TiO_2$
(3) Zeolites
    alkali ion-exchanged zeolites: Na—X, Cs—X
    alkali ion-added zeolites: $Cs_2O$/Cs—X
(4) Supported alkali metal Compounds
    alkali metal compounds on alumina: $Na^0/Al_2O_3$, $Na_2O/Al_2O_3$
    alkali metal compound on silica; $Na^0/SiO_2$, $Na_2O/SiO_2$
    alkali metal ions on alkaline earth oxides: $Na_2O$/MgO
(5) Clay minerals
    hydrotalcite: $Mg_6Al_2(OH)_{16}CO_3 \cdot 4H_2O$
    chrysolite: $Mg_3(Si_2O_5)O_3(OH)_4$
    sepiolite: $Mg_4Si_6O_{15}(OH)_2$
(6) Non-oxide
    KF supported on alumina: $KF/Al_2O_3$
    lanthanide imide and nitride on zeolite
    metal oxynitrides: ALPON, VALPON Base catalysts usually include metal oxides and clay minerals. Hydrotalcite, alkaline earth metal oxides, supported alkali metal compounds and zeolites are examples of catalysts with basic sites on surface. Table 1 is a list of different types of solid base catalysts. Many solid base-catalyzed reactions initiate with an abstraction of $H^+$ from a molecule by basic sites. Double bond isomerization of olefins, dehydration of alcohols and hydrogenation of olefins are fundamental base catalyzed reactions. Table 2 summarizes industrial applications of base catalysts.

TABLE 2

Industrial applications of solid base catalysts (Hattori 2014).

| Reaction | Catalyst | Year |
|---|---|---|
| Alkylation | | |
| Alkylation of phenol with methanol | MgO | 1970, 1985 |
| Alkylation of xylene with butadiene | $Na/K_2CO_3$ | 1995 |
| Alkylation of cumene with ethylene | $Na/KOH/Al_2O_3$ | 1988 |

TABLE 2-continued

Industrial applications of solid base catalysts (Hattori 2014).

| Reaction | Catalyst | Year |
|---|---|---|
| Isomerization | | |
| Isomeriziation of safrole to isosafrole | Na/NaOH/$Al_2O_3$ | 1988 |
| Isomerization of 2,3-dimethyl-1-butene | Na/NaOH/$Al_2O_3$ | 1988 |
| Isomerization of 3,5-vinylbicyclo[2,2,1]heptane | Na/NaOH/$Al_2O_3$ | 1988 |
| Isomerization of 1,2-propadine to propyne | $K_2O$/$Al_2O_3$ | 1996 |
| Dehydration/condensation | | |
| Dehydration of 1-cyclohexylethanol | $ZrO_2$ | 1986 |
| Dehydration of propylamine-2-ol | $ZrO_2$/KOH | 1992 |
| Isobutyraldehyde to diisopropyl ketone | $ZrO_2$ | 1973 |
| Dehydrotrimerization of isobutyraldehyde | BaO—CaO | 1995 |
| Esterification | | |
| Esterification of ethylene oxide | Hydrotalcite | 1994 |
| Transesterification of triglycerides | ZnO—$Al_2O_3$ | 2006 |
| Miscellaneous | | |
| Carboxylic acids to aldehydes | $ZrO_2$—$Cr_2O_3$ | 1988 |
| Thiols from alcohols with hydrogen sulfide | Alkali/$Al_2O_3$ | 1988 |
| Cyclization of imine with sulfur dioxide | Cs-zeolite | 1995 |

Basicity of the reaction medium plays an important role in catalytic production of methacrylic acid from itaconic acid and citric acid (Carlsson et al. 1994). The rate of decarboxylation of itaconic acid and citric acid is dependent on the pH of the reaction. The itaconate monoanion decarboxylates faster than the protonated and neutral itaconic acid (Li and Brill, 2001). Adding base to the reaction medium also increases the selectivity of methacrylic acid (Carlsson et al. 1994). At low pH, methacrylic acid starts degrading by addition of water molecules to double bonds (acid-catalysed reaction). Le Nôtre et al. 2014 reported an optimum amount of base in the reaction medium where methacrylic acid selectivity reaches to its highest value. FIG. 3 shows the results of Pd-catalysed itaconic acid decarboxylation with different amounts of base.

In FIG. 3 the solid line (isomers conversion) refers to conversion of mesaconic acid and citraconic acid which are in fast equilibrium with itaconic acid. FIG. 3 indicates a maximum methacrylic acid and minimum byproducts selectivity at 1 equivalent of sodium hydroxide. The same results were obtained with other types of base which verifies that the effect of adding base is due to change of pH and not presence of ions. Decarboxylation, the removal of carbon dioxide from the carboxyl group, can be performed by using heat and a catalyst. An organic chemical reaction usually requires one or more chemical steps to produce a specific substance. For example, citric acid requires one dehydration step, followed by two decarboxylation step and itaconic acid only needs one decarboxylation step to produce methacrylic acid (shown in FIG. 2). Transition-metal catalysts such as platinum and palladium have been used in decarboxylation processes. Pt/C was used to decarboxylate fatty acids at 330° C. (Fu et al., 2011) and Pd/C was used in decarboxylation of alkyl carboxylic acids in water at 250° C. and 40-50 bar (Matsubara et al., 2004). Pd catalysts have been also used in decarboxylation of glutamic acid and pyroglutamic acid to bio-based 2-pyrrolidone. Recently Le Nôtre et al. 2014 has reported the use of Pd/C and Pt/C in decarboxylation of citric acid and itaconic acid to methacrylic acid at 250° C. Besides solid transition-metal catalysts, it has been reported that hydrotalcite can be employed in decarboxylation of fatty acids (Na et al., 2010). This solid base catalyst has been tested for decarboxylation of oleic acid with three different MgO contents. Hydrotalcite is a layered anionic clay with base sites originating from $HCO^-_3$ on the hydrophilic surface. Higher MgO contents resulted higher oleic acid conversion.

The production of bio-based methacrylic acid can be possible to achieve in one step under relatively mild conditions from fermentation-derived itaconic acid. Some *Aspergillus* species, like *A. itaconicus* and *A. terreus*, show the ability to synthesize itaconic acid. Since the 1960s the production of itaconic acid is achieved by the fermentation with *Aspergillus terreus* on sugar containing media (Willke and Vorlop, 2001). *A. terreus* is still the main production host of itaconic acid, because so far only bred strains of this species can reach levels of up to 80-86 g/L (Kuenz et al., 2012). Bentley and Thiessen 1957 proposed a pathway for the biosynthesis of itaconic acid (FIG. 4). Starting from a sugar substrate like glucose the carbon molecules are processed via glycolysis to pyruvate. Then the pathway is split and part of the carbon is metabolized to Acetyl-CoA releasing a carbon dioxide molecule. The other part is converted to oxaloacetate so that the previously released carbon dioxide molecule is again incorporated. In the first steps of the citric acid cycle, citrate and cis-aconitate are formed. In the last step, the only itaconic acid pathway dedicated step, cis-aconitate decarboxylase (CadA) forms itaconic acid releasing carbon dioxide. The main components of itaconic acid fermentation medium are carbohydrate, ammonium, nitrate, phosphate and other trace minerals. The important limitation in the direct catalytic conversion of biologically derived molecules is the nature of the impurities present in the feedstock. Catalyst activity, stability and selectivity can be challenging issues in the reaction medium because of the complex nature of these molecules. Catalyst poisoning is an issue that can occur due to the presence of components like ammonium, trace minerals and nitrate in the fermentation medium.

Few studies have focused on the impact of the impurities that originate from fermentation medium on heterogeneous catalysts. Miller et al. 2008 reported loss of activity for Ru-catalyzed hydrogenation of fermentation-derived lactic acid due to the presence of amino acids and proteins in fermentation medium. In a study by Elliott et al. 2004 on Ru and Ni-catalyzed hydrogenation of sugars, ammonium showed a significant inhibition effect on the catalysts. Sulfonic acid-containing carbon catalysts for the esterification of succinic acid also show loss of activity due to the adsorption of organic species on the catalyst (White et al., 2009). As far as catalyst activity is concerned, the potential problem components in fermentation medium can be sulfate (potential for metal sulfide formation); calcium, magnesium, and phosphate (potential for catalyst pore plugging by insoluble salt precipitation); sodium or potassium (alkali attack on the catalyst support); organic nitrogen components, such as amino acids (thiol source for metal sulfide formation), proteins (pore plugging by precipitation of denatured forms), or urea (metal complex formation); chloride (reaction with the metal). Sulfur is a known compound in poisoning of palladium catalysts (Albers et al., 2001). Studies on $SO_2$/Pd interactions on three-way catalysts show that the poisoning of the Pd component was partly irreversible due to direct interactions between Pd and $SO_2$ (Beck and Sommers, 1995). An additional impact of the presence of water was believed to be competitive action between water and SO$_2$ which was dependent on temperature. Hydrogen treatment of sulphur-poisoned supported Pd-complex catalysts used in selective hydrogenation of styrene to ethylbenzene was shown to be able to partially eliminate the sulfur compound (L'Argentière et al., 1997). Protein components in biomass feedstocks can lead to formation of peptide fractions (from hydrolysis) or ammonium ions (from more severe breakdown), both of which might interfere with catalysis.

Water is a safe, readily available and environmentally friendly compound that can be used as a solvent and reaction medium where possible. Subcritical water is liquid water under pressure at temperatures between boiling point and critical temperature. In recent years, subcritical water has received a great attention because its properties vary as temperature increases. Many of these irregular properties at increased temperature are due to very strong hydrogen bonding. For instance, the dielectric constant of water decreases with increasing temperature due to the steady decrease in the effectiveness of hydrogen bonds (Kus, 2012). Above the subcritical point (critical point is at 374° C. and 22.064 MPa), water becomes less polar and starts behaving like an organic solvent. Hence, organic molecules show an increase in solubility in water as the temperature rises. On the other hand, the ion product is an interesting parameter in high temperature water. Increasing the temperature of liquid water can alter the ion concentrations. This enhanced acidity/basicity from the increased ion product makes hot liquid water an interesting medium for acid/base catalyzed reactions. The hydrolysis of some ethers and esters in neutral hot liquid water has been reported due to the high ion product of hot liquid water. Taylor et al. proposed a hydronium ion-catalyzed mechanism for hydrolysis of methyl t-butyl ether. Patrick et al. also reported a mechanism for methyl benzoate hydrolysis that also uses hydronium ion from water as the catalyst.

Hot liquid water has also been employed in decarboxylation processes. Unsubstituted indoles have been produced by removal of 2-carboxyl group with methods like pyrolysis or heating with various derivatives of copper, in quinolone. However, by using hot liquid water, Indole-2-carboxylic acid is decarboxylated after 20 minutes at 255° C. in water (Scheme 1).

Scheme 1. Decarboxylation reaction of Indole-2-carboxylic acid in high temperature liquid water (An et al., 1997)

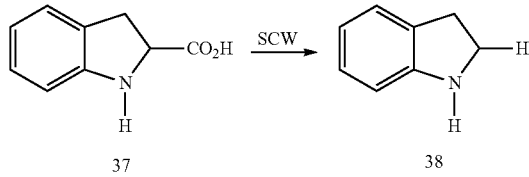

In another study ester was hydrolyzed for 6 hours at 290° C. and the product was decarboxylated to give styrene in 69% yield. Alkylation, condensation, isomerization are other examples of catalysis at hot liquid water (An et al., 1997).

Catalytic decarboxylation of itaconic acid is a possible bio-based route for production of methacrylic acid. Literature review analysis indicates use of transition-metal catalysts such as palladium and platinum in production of methacrylic acid from itaconic acid. The importance of reaction medium basicity in decarboxylation of itaconic acid to methacrylic acid was also discussed above. For example, homogeneous base catalysts like sodium hydroxide were used to achieve higher methacrylic acid selectivity. However, application of homogeneous base catalysts in chemical processes causes severe problems such as corrosion of reactors, difficult separation and recycling of the catalyst, high costs of waste disposal and wastewater treatment.

In order to reduce these problems, heterogeneous base catalysts can be promising replacements for homogeneous base catalysts in industry. Since transition-metal catalysts and homogeneous base catalysts were used simultaneously to achieve higher methacrylic acid yield and selectivity, it is hypothesized that synthesizing a solid base catalyst impregnated with a transition-metal catalyst will increase methacrylic yield and selectivity in decarboxylation of itaconic acid. Previous results from studying the effect of itaconic acid residence time on methacrylic acid yield in presence of homogeneous base catalyst verifies that methacrylic acid yield rises rapidly to almost a steady state value (Carlsson et al. 1994). So the methacrylic acid yield value in shorter residence times is approximately equal to the methacrylic acid yield value in longer residence times. These promising results lead us to design a process in order to produce methacrylic acid continuously using solid base catalysts.

The aim of this study is to determine the kinetics of methacrylic acid formation over solid base catalysts such as hydrotalcite. Citric acid and citramalic acid are other fermentation derived compounds that can be converted to methacrylic acid. Citric acid requires one step dehydration followed by two step decarboxylation and citramalic acid requires one step decarboxylation and one step dehydration. The decarboxylation procedure using hydrotalcite is also applicable to these carboxylic acids.

The main objectives of this project are as follows:

To determine the substrate conversion and methacrylic acid yield and selectivity achieved by different solid-base catalysts;

To synthesize a solid-base catalyst impregnated with a transition metal and determine the effect of adding a transition metal to solid-base catalyst on methacrylic acid yield and selectivity;

To perform a comprehensive catalyst characterization on the synthesized solid-base catalyst loaded with transition metal;

To determine the effect of calcination temperature and MgO/Al$_2$O$_3$ ratio on hydrotalcite activity;

To determine the kinetics of methacrylic acid formation from carboxylic acids such as itaconic acid and citric acid over different temperatures, residence times, catalyst weight and substrate concentrations;

To determine the possibility of methacrylic acid formation from carboxylic acids using solid-base catalysts continuously;

To determine the impact of key components in fermentation medium of substrate on catalyst activity; and/or To determine the reusability of the catalysts.

These and other objectives are met in whole or in part by the present disclosure.

BRIEF SUMMARY

An embodiment of the present disclosure includes a method of producing methacrylic acid comprising contacting 2-hydroxyisobutyric acid (HIB) and/or itaconic acid and/or citric acid and/or citramalic acid, or one or more salts thereof, with a catalyst comprising a hydrotalcite under conditions sufficient to produce methacrylic acid.

Another embodiment includes a composition comprising a transition metal e.g., palladium, platinum, rhodium, and the like or a salt thereof, e.g., palladium nitrate and a hydrotalcite solid comprising pores, wherein the transition metal or salt thereof is adsorbed in or on the pores.

Another embodiment includes the use of a palladium on hydrotalcite catalyst to produce methacrylic acid from 2-hydroxyisobutyric acid and/or itaconic acid and/or citric acid and/or citramalic acid, or one or more salts thereof.

Another embodiment includes the use of a hydrotalcite to produce methacrylic acid from 2-hydroxyisobutyric acid and/or itaconic acid and/or citric acid and/or citramalic acid, or one or more salts thereof Another embodiment includes the use of subcritical water to produce methacrylic acid from 2-hydroxyisobutyric acid and/or itaconic acid and/or citric acid and/or citramalic acid, or one or more salts thereof.

DETAILED DESCRIPTION

Figure 1:
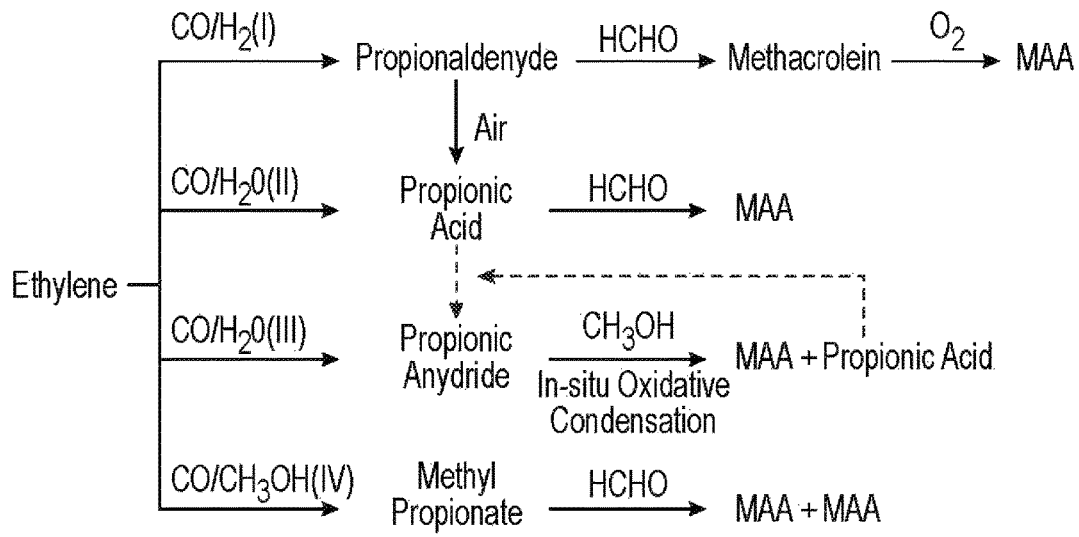
FIG. 1 describes $C_2$ carbonylation technologies in methacrylic and methyl methacrylate production as described by Spivey et al., 1997

In the description and claims of the present application, each of the verbs, "comprise", "include" and "have", and conjugates thereof, are used to indicate that the object or objects of the verb are not necessarily a complete listing of members, components, elements, or parts of the subject or subjects of the verb.

The production method may be carried out in an inert gas, for example, nitrogen, helium, or argon. The method may be carried out in subcritical water or in supercritical water. The production method may be carried out in anhydrous conditions in an appropriate organic solvent.

The production method may carried out at a temperature of from about ambient temperature to about 700° C., or from about 50° C. to about 500° C., or from about 100° C. to about 400° C. or from about 200° C. to about 300° C.

The production method may be carried out at a pressure of from about ambient pressure to about 1000 psi (pounds per square inch), or from about 100 psi to about 1000 psi, or from about 200 psi to about 700 psi, or from about 250 psi to about 500 psi.

The production method may be carried out in a batch or continuous mode.

The production method may be carried out with "residence time" i.e, a time a reaction mixture is in contact with the catalyst, is from about 0.5 min to about 60 min, or from about 1 min to about 45 min, or from about 1 min to about 30 min, or from about 1 min to about 15 min, or from about 15 min to about 30 min.

The concentration of acid precursor in a reaction vessel may be from about 1 to about 100 g/L or from about 2 to about 50 g/L, or from about 3 to about 50 g/L, or from about 5 to about 20 g/L, or from about 5 to about 10 g/L, or from about 10 to about 20 g/L.

The amount of catalyst that may be utilized may range from about 0.1 g to about 1 g using the concentrations of acid precursor and may depend on whether the reaction is run as a batch or as a continuous process.

The catalyst turnover number (moles of acid converted per mole of catalyst) may be from about 10 to about $10^6$, or from about 10 to about $10^6$, or from about 100 to about $10^5$ or from about 100 to about $10^4$.

In order to determine the kinetics of methacrylic acid formation over a solid base catalyst, hydrotalcite (clay mineral) will be employed as reaction catalyst. Hydrotalcite impregnated with palladium catalyst will be also synthesized, since the use of both transition-metal catalysts and base catalysts in decarboxylation of itaconic acid to methacrylic acid is discussed in literature review analysis. Each catalyst will be used to catalyze the decarboxylation of itaconic acid and citric acid and citramalic acid. These substrates are used in order to have an organic decarboxylation reaction since itaconic acid only needs one decarboxylation step to produce methacrylic acid and citric acid requires one step dehydration followed by two step decarboxylation and citramalic acid requires one step decarboxylation followed by one step dehydration. A kinetic study of decarboxylation reaction over different amounts of catalysts, concentrations of substrate and residence times will be performed in a series of batch reactors. Yield, conversion and selectivity achieved by each catalyst will be determined. Hence, the results of each experiment will help us to find an optimum temperature, substrate concentration and residence time point for the highest methacrylic acid selectivity and yield. Table 3 shows different reaction conditions that are going to be tested.

TABLE 3

Reaction Variables

| | |
|---|---|
| Temperature | 200-250° C. |
| Pressure | 500 psi |
| Inert Gas | Helium |
| Residence Times | 1-15-30 min |
| Carboxylic Acid Concentrations | 5-10-20 gr/lit |
| Catalyst Weight | 0.125-0.25-0.5-1-2 gr |

Figure 5:
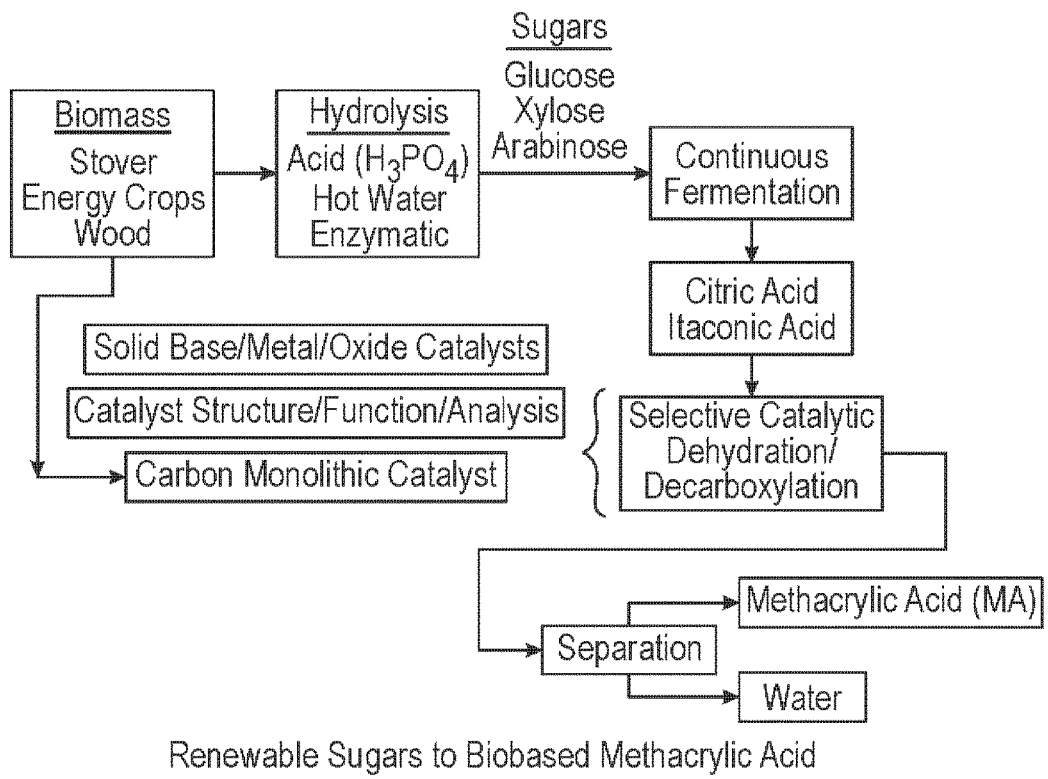
FIG. 5 is a schematic diagram showing a manner of converting renewable sugars to biobased methacrylic acid.
Figure 6:
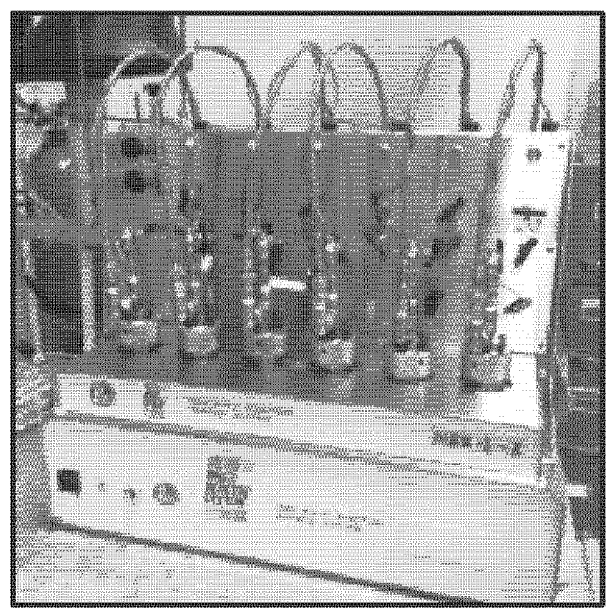
FIG. 6 shows a picture of a PARR 5000 Multiple Reactor System.

Production of methacrylic acid is performed in the 75 mL vessel of a PARR 5000 Multiple Reactor System. The vessel is loaded with 40 mL of substrate solution in deionized water and catalyst that are mixed using a magnetic stir bar, inside the vessel. The vessel is sealed using the vessel cap with six screws. The mixture is stirred with a magnetic bar stirrer at 750 rpm. The headspace of the vessel is charged with 500 psi of helium through a needle valve. The vessel is heated using a heating well at an average heating rate of 9° C./min. The temperature is measured by a thermocouple in an alloy thermowell (FIG. 5). Once the reaction is completed, the vessel is cooled down using a water bath at room temperature. The stirrer bar is allowed to agitate during heat-up. After taking gas sample (using 1 liter Tedlar bag), the headspace pressure is released through a second needle valve. The catalyst is removed from the liquid product using filter paper.

Methacrylic acid and byproducts concentrations (liquid sample) are determined using High Performance Liquid Chromatography (HPLC). HPLC (Shimadzu LC-20 AT) is performed by using an autosampler and pump with 7 mN $H_2SO_4$ eluent and 0.6 mL/min flow at 60° C. Methacrylic acid peak is verified with UV detection at 210 nm. The sample injection volume and run time are 5 microliter and 30 minutes, respectively. Coregal 64-H transgenomic column (7.8×300 mm) is used in this instrument. Gas Chromatography—Thermal Conductivity Detection (GC-TC Hewlett Packard 5890 Series II) is performed for gas analysis with the inlet temperature of 100° C., initial oven temperature of 35° C. and detector temperature of 140° C. The initial 5 minutes holding time, followed by a ramp of 20° C./min for 8.25 minutes and final holding time of 5.75 minutes at 200° C. is used as the method for gas analysis. The volume of each injection is 50 microliter. The concentration of each compound is determined with standard curves on HPLC and GC-TCD. Since the main reaction is decarboxylation, $CO_2$ and propene (result of methacrylic acid degradation) are expected in gas samples. The standard curve for $CO_2$ was performed using nitrogen as the balance gas. 5, 10, 25, 50 and 75 percent by volume $CO_2$ (run in triplicate) was used to make the standard curve on GC-TCD. Methacrylic acid, mesaconic acid, citraconic acid, acetone, acetic acid, pyruvic acid, citric acid and itaconic acid standard curves were made using deionized water as the solvent. 5 different concentrations of each compound based on g/lit were used to make the standard curve on HPLC.

Methacrylic acid and byproducts concentrations (g/lit) are determined using High Performance Liquid Chromatography (HPLC). Considering that the volume of reaction is 40 ml, moles of each compound are calculated through molar weight. In order to calculate yield and selectivity of each compound and conversion of reaction substrate the following equations are used.

$$\% \text{ Yield of Compound } i = \frac{\text{Moles of Compound } i \text{ Generated}}{\text{Moles of Substrate Charged}} * 100 \quad \text{Eq. (1)}$$

$$\text{Conversion of Substrate } (X) = \frac{\text{Moles of Substrate Reacted}}{\text{Moles of Substrate Charged}} \quad \text{Eq. (2)}$$

$$\% \text{ Selectivity of Methacrylic Acid} = \frac{\text{Moles of Methacrylic Acid Generated}}{\text{Total Moles of Undesired Byproducts}} * 100 \quad \text{Eq. (3)}$$

Gas Chromatography—Thermal Conductivity Detection (GC-TC) is performed for gas analysis. Gas samples are taken after the reactor is cooled down at room temperature. 50 microliter of each gas sample is injected on GC-TCD. Percent $CO_2$ (by volume) of each sample is calculated using the peak area and standard curve of $CO_2$. In order to calculate the number of carbon dioxide moles, total moles of gas in the reactor is calculated using ideal gas law. The total moles of gas multiplied by percent $CO_2$ will give the number of $CO_2$ moles:

$$n_{CO2} = \frac{PV}{RT} * \% \text{ CO2} \quad \text{Eq. (4)}$$

P=Reactor Pressure
V=Reactor Headspace Volume
R=Universal Gas Constant 8.314 J/K·mol
T=Temperature of The Gas after cool-down

EXAMPLES

Example 1: Hydrotalcite and Pd/Hydrotalcite Synthesis

The raw hydrotalcite (HTC) powder with $MgO/Al_2O_3$ ratio=4.0-5.0 (purchased from Sigma-Aldrich) was calcined at 400° C. overnight and then allowed to cool. It was stirred in deionized water to make a paste, and the paste was placed in a 105° C. degree drying oven over night. Then the dried hydrotalcite was smashed and sieved to a particle size between 1 mm and 0.5 mm.

Example 2: Palladium on Hydrotalcite Preparation

Literature review analysis indicates use of transition-metal catalysts such as palladium and platinum in production of methacrylic acid from itaconic acid. The importance of reaction medium basicity in decarboxylation of itaconic acid to methacrylic acid was also discussed in the background and literature analysis chapter. Therefore a solid-base catalyst impregnated with a transition metal will be synthesized with the purpose of increasing methacrylic acid yield in decarboxylation of carboxylic acids such as itaconic acid. Pd/HTC will be prepared using incipient wetness impregnation (Nikolopoulos et al., 2005). Incipient wetness impregnation is a technique for the synthesis of heterogeneous catalysts. The active metal precursor is dissolved in aqueous solution. Then the metal containing solution is added to the catalyst support containing the same pore volume as the volume of the solution that was added. Capillary action draws the solution into the pores. In our case, a 5 wt. % palladium (II) nitrate dihyrate (40% Pd basis, Sigma-Aldrich) solution in deionized water will be prepared. Nikolopoulos et al. 2005 used palladium chloride salt for impregnating hydrotalcite catalyst. Since chloride can have a poisoning effect, the nitrate salt is used in our study. After adding the solution to the hydrotalcite powder (containing the same pore volume as the volume of the solution that is added), The catalyst will be dried at 120° C. for two hours, calcined at 400° C. for two hours and then crushed and sieved to the desired particle size. Total pore volume of the catalyst is measured using nitrogen desorption curves with BJH analysis. Prior to reaction the sample will be reduced at 450° C. for 8 hours in flowing 100% hydrogen (Nikolopoulos et al., 2005).

Example 3: Decarboxylation of Citric Acid

Decarboxylation process is also applicable to citric acid, a more widely available bio-based substrate. Citric acid requires one dehydration step, followed by two decarboxylation steps to result methacrylic acid. The kinetics of methacrylic acid formation from citric acid over varying temperatures, and catalysts were studied. The reactions were performed at temperatures of 200, 225, 250° C. and for one hour residence time. The feedstock solution contains 20 g/lit citric acid and 0.15 mol/lit NaOH. The effect of adding NaOH in experiments is due to a change in pH. pH of the medium effects on methacrylic acid selectivity. At low base concentrations, methacrylic acid degradation can also occur due to acid-catalysed addition of water molecules across the double bonds. The initial series of experiments were performed with hydrotalcite, Pd/C (5 wt. %-Alfa Aesar) and synthesized iron oxide/C catalysts.

Example 4: Deposition of Iron Oxide Nanoparticles in Activated Carbon

Using iron containing catalysts in catalytic decarboxylation has been reported. Zhang et al. reported catalytic decarboxylation of fatty acids by iron-containing minerals. For the purpose of decarboxylation reaction, iron oxide catalyst was prepared using the following procedure: 150 ml of Fe(NO3)3.9H2O (SIGMA-ALDRICH, ACS reagent of minimum purity 98 wt. %) Solution (0.5 M) was made with deionized water. 30.3 g activated carbon (SIGMA-ALDRICH, Norit RO 0.8) pellets were allowed to soak in the solution. The solution was subjected to sonication treatment for 45 minutes at room temperature. After five days of soaking, the mixture was divided into three batches (each 10.1 grams of activated carbon and 50 ml of the solution). Each batch was treated under helium gas in the high pressure micro reactor system. Starting pressure was 750 psi to the final pressure of 4050 psi. Starting temperature was 17° C. and final temperature was 355. The mixture was maintained at 355° C. for 90 minutes. Finally the reactor was cooled down to 33° C. The activated carbon pellets were separated from the mixture and washed several times with deionized water and dried overnight in the oven (Xu and Teja, 2006).

Figure 7:
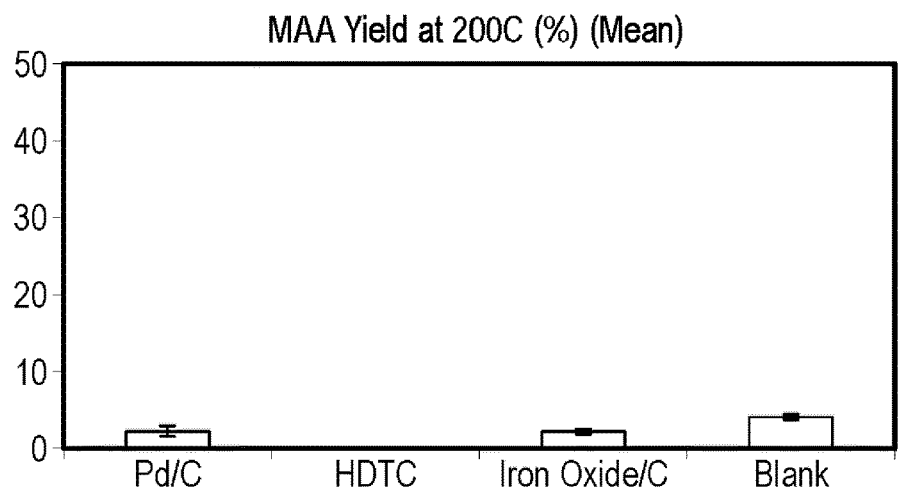
FIG. 7 is a graph of MAA yield at 200° C. under reaction conditions of 20 gr/lit citric acid+0.15 M NaOH, 1 g catalyst for 1 hr
Figure 8:
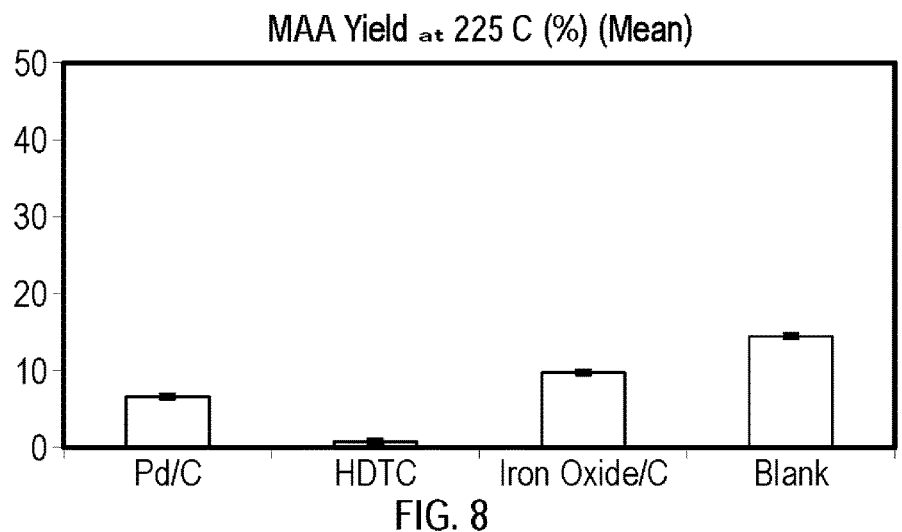
FIG. 8 is a graph of MAA yield at 225° C. under reaction conditions of 20 g/lit citric acid+0.15 M NaOH, 1 g catalyst for 1 hr.

FIG. 7 shows that at 200° C. methacrylic acid yield, in presence of hydrotalcite, is zero. Results of control experiments indicate higher yields of methacrylic acid in comparison with catalytic experiments at 200° C. FIG. 7 and FIG. 8 also suggest the same trend for methacrylic acid formation from citric acid at higher temperatures. The results verify that methacrylic acid yield increases with increasing the temperature in both blank and catalytic experiments.

Unfortunately, we were not able to repeat Le Nôtre et al., 2014 results (65% MAA yield) with palladium on carbon catalyst and none of the other catalysts worked in the decarboxylation process of citric acid in presence of sodium hydroxide.

Figure 9:
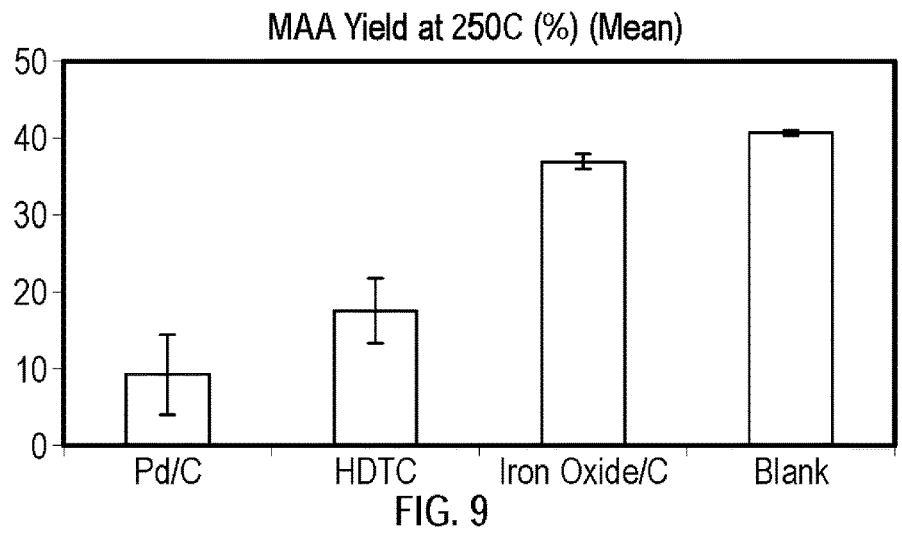
FIG. 9 is a graph of MAA yield at 250° C. under reaction conditions of 20 g/lit citric acid+0.15 M NaOH, 1 g catalyst for 1 hr.
Figure 10:
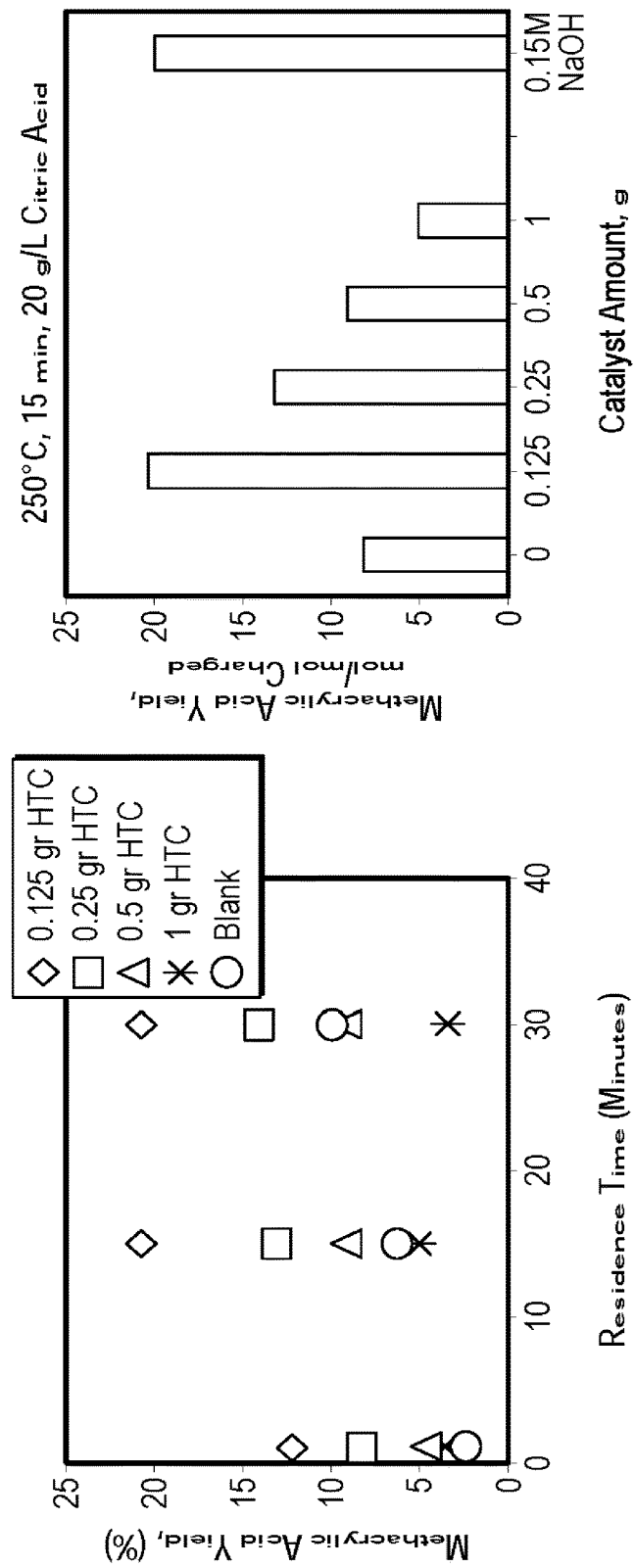
FIG. 10 is a graph of MAA yield at 250° C. (Substrate: 20 g/lit citric acid+No base).
Figure 11:
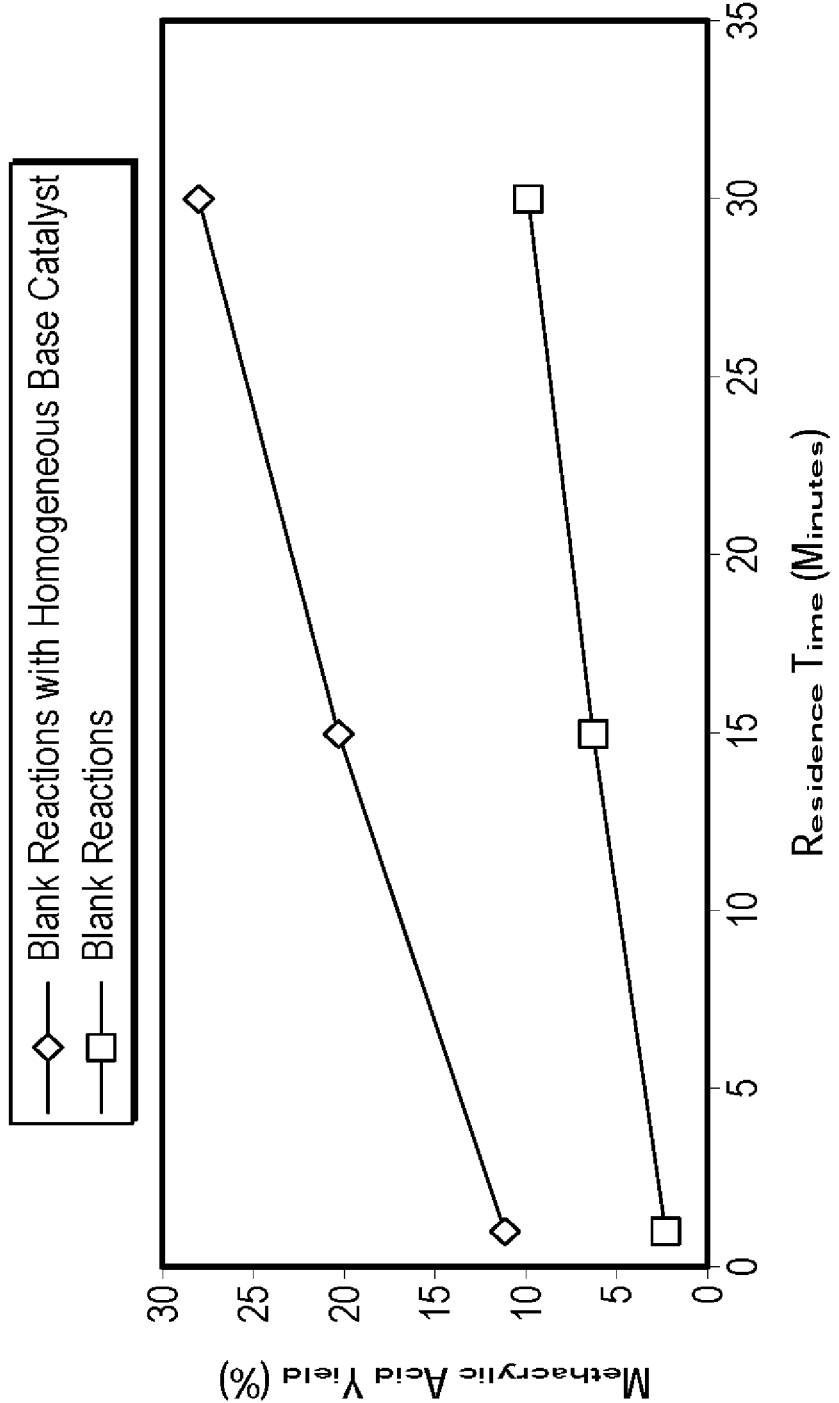
FIG. 11 is a graph of a comparison between blank reactions with and without sodium hydroxide (250° C. with 0.15M NaOH and 20 g/lit citric acid.

Since hydrotalcite is a solid-base catalyst, a set of experiments with no base in reaction medium at different residence times using different amounts of hydrotalcite were also performed on citric acid. The results, shown in FIG. 10, indicate that methacrylic acid yield increases with decreasing the amount of catalyst in the reaction medium. The highest and the lowest methacrylic acid yield were achieved at 0.125 g and 1 g amount of hydrotalcite, respectively. It is notable that blank reactions had lower methacrylic acid yields than almost all of the catalytic reactions except for 1 gram hydrotalcite runs. From FIG. 9 and FIG. 10, it is obvious that adding both homogeneous and heterogeneous catalysts increases the methacrylic acid yield. The 1 minute residence time experiments show promising results for production of methacrylic acid continuously.

Example 5: Decarboxylation of Itaconic Acid

Figure 2:
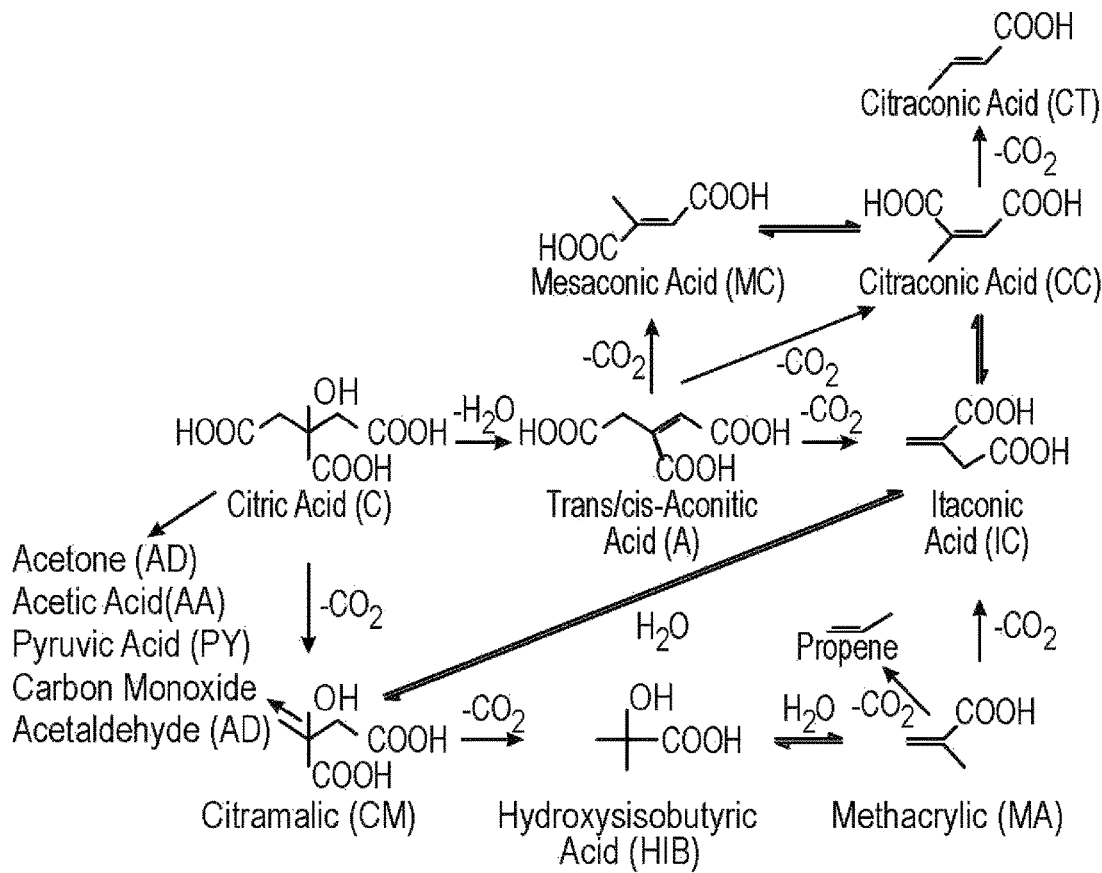
FIG. 2 describes pathways for decomposition of citric acid in hot liquid water as described by Carlsson et al., 1994.
Figure 3:
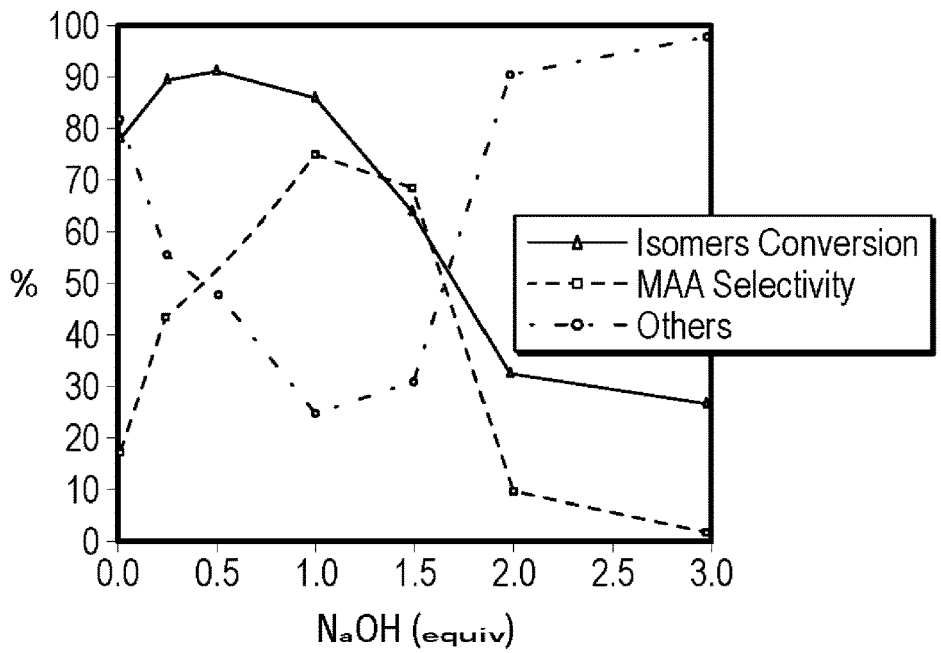
FIG. 3 describes a Pd-catalysed itaconic acid decarboxylation with different amounts of NaOH wherein the reaction conditions are 0.15M itaconic acid, 250° C., 1 hr residence time as described by Le Nôtre et al., 2014.
Figure 4:
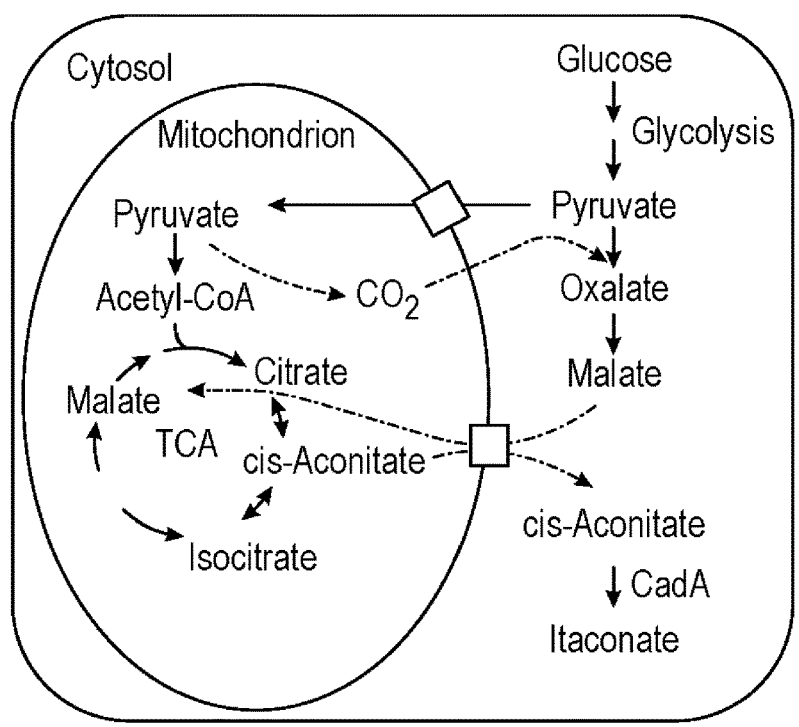
FIG. 4 shows a scheme describing a biosynthesis pathway of itaconate and its compartmentalization between cytosol and mitochondrion in the *A. terreus* cell; note: cis-aconitate transport is speculative as described by Steiger et al., 2013.

Formation of methacrylic acid from citric acid requires one dehydration step followed by two decarboxylation steps (FIG. 2). Itaconic acid can form methacrylic acid with only one decarboxylation step. Hence a set of experiments with no base in reaction medium at different residence times using different amounts of hydrotalcite were also performed on itaconic acid.

Figure 12:
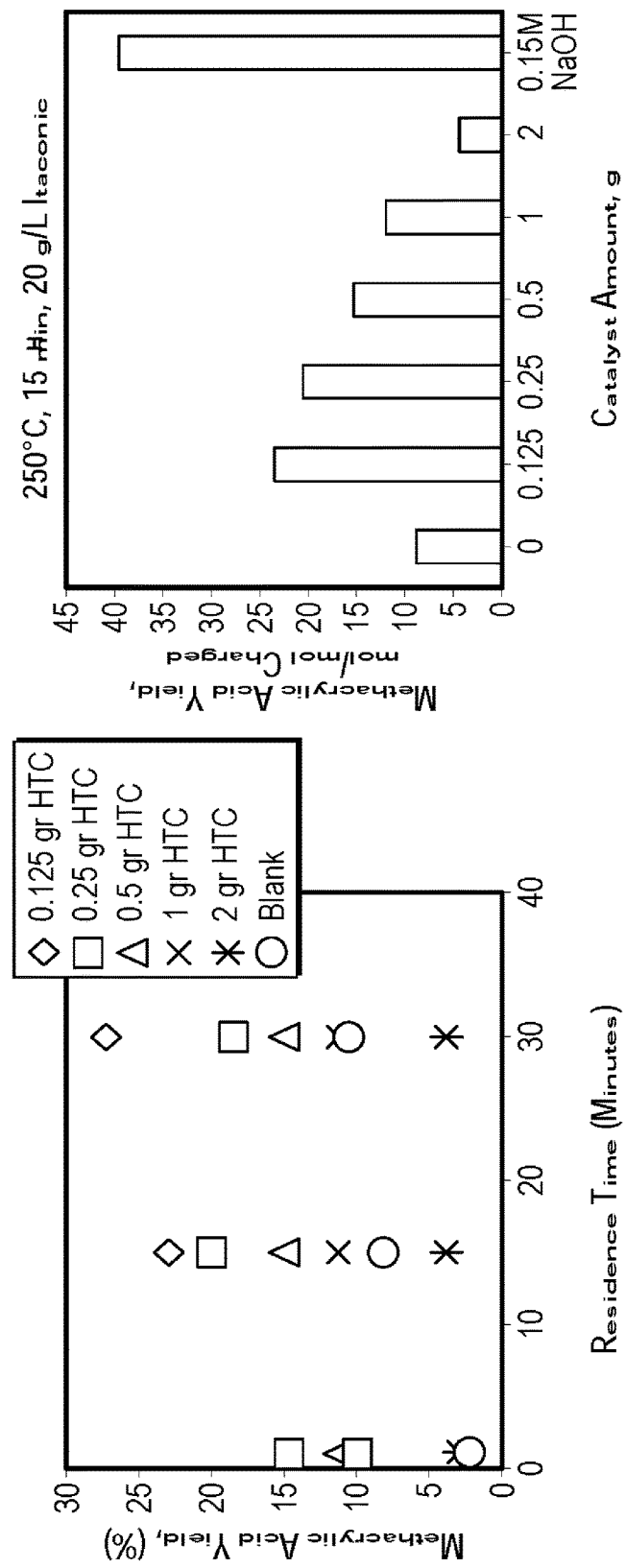
FIG. 12 is a graph of MAA yield at 250° C. (Substrate: 20 g/lit itaconic acid+No base)
Figure 13:
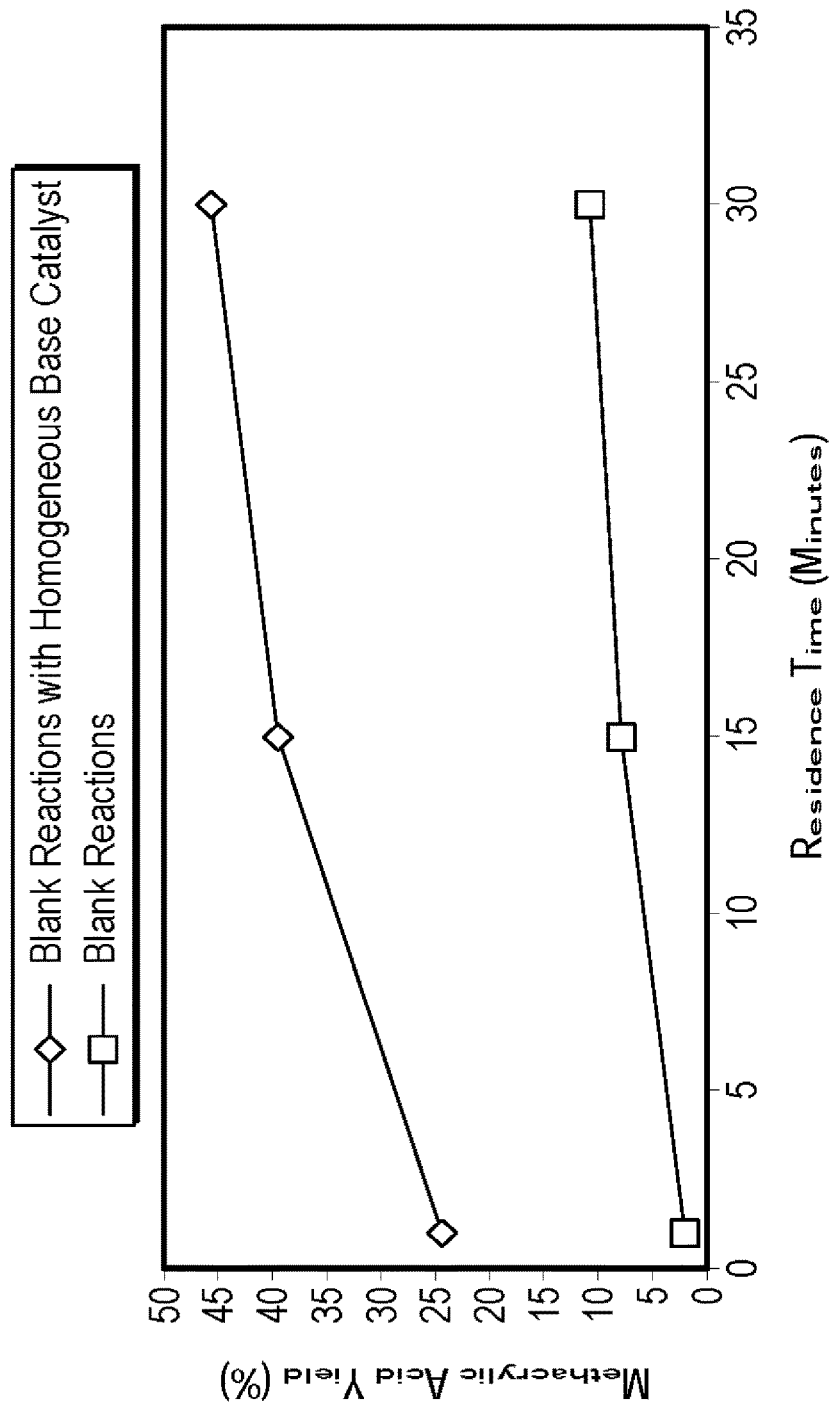
FIG. 13 is a graph of a comparison between blank reactions with and without NaOH (250° C. 0.15M NaOH-20 g/lit itaconic acid)
Figure 14A:
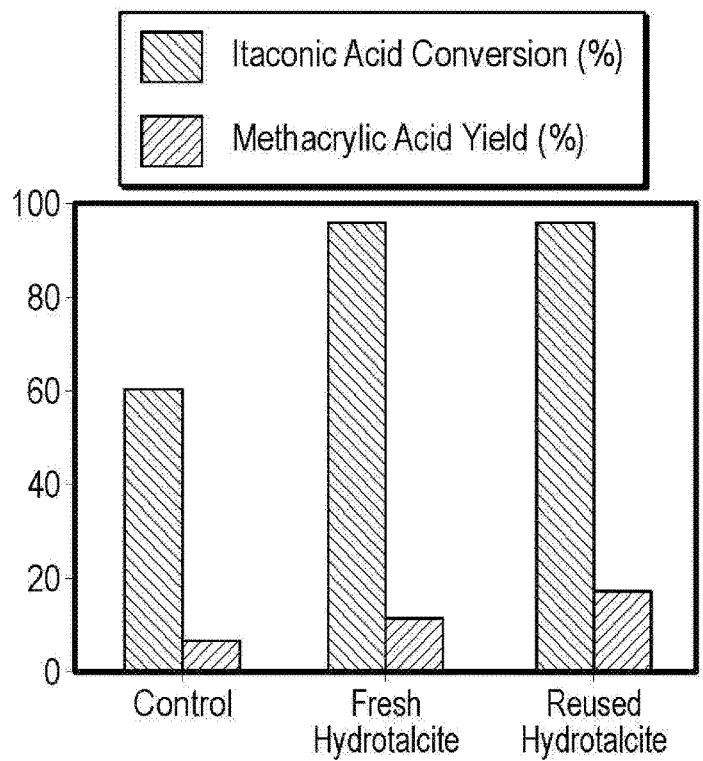
FIG. 14A and FIG. 14B are a set of graphs showing catalyst reuse results (1 g fresh hydrotalcite-0.92 g recovered hydrotalcite-250° C.-20 g/lit itaconic acid-15 minutes).
Figure 14B:
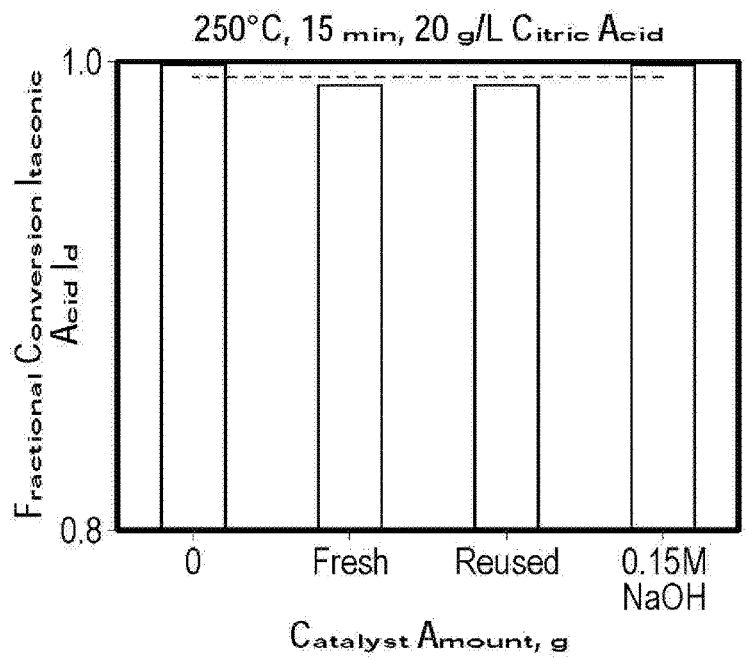
Figure 14C:
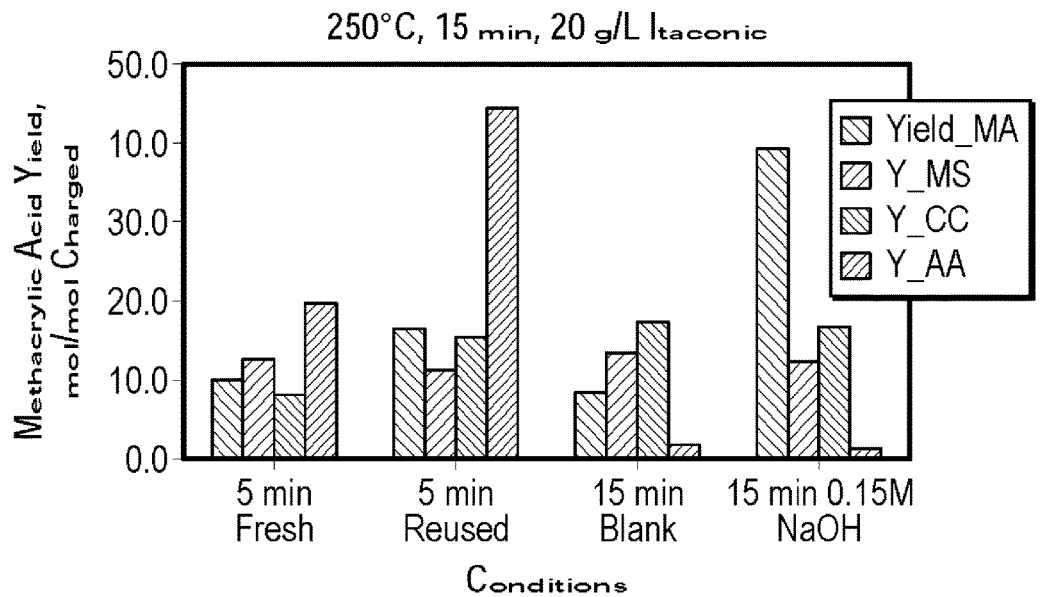
FIG. 14C and FIG. 14D are a set of graphs showing catalyst reuse results (1 g fresh hydrotalcite—0.70 g recoverd hydrotalcite—250° C.-20 g/lit citric acid-5 minutes)—wherein the abbreviations have the following meanings: MA is methacrylic acid, MS is mesaconic, CC is citraconic, IT is itaconic, and AA acetic acid.
Figure 14D:
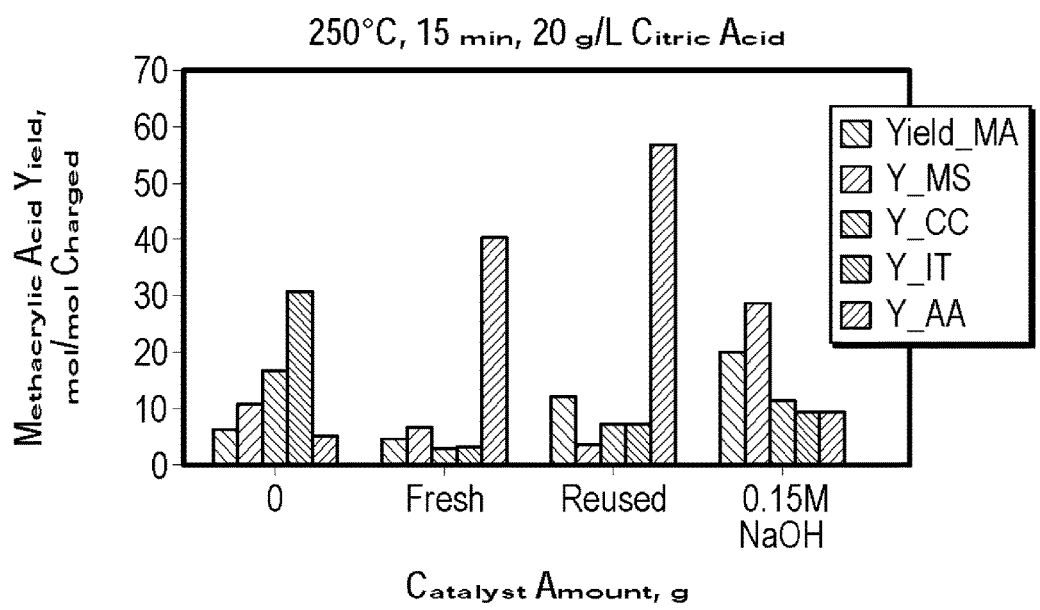

Methacrylic acid yield also increases with decreasing amounts of catalyst using itaconic acid as the reaction substrate. The highest methacrylic acid yield was achieved at 0.125 g catalyst (the same trend as citric acid reactions). The results of both citric acid and itaconic acid experiments suggest an optimum amount of solid-base catalyst for the highest methacrylic acid yield. In order to compare methacrylic acid yield in blank reactions and reactions with homogeneous base catalysts, 0.15 M sodium hydroxide was added to the reaction medium. Adding sodium hydroxide to the reaction medium also caused an increase in methacrylic acid yield (FIG. 12 and FIG. 13).

Example 6: Catalyst Reuse

In order to study the reusability of catalysts, the catalysts were recovered after the reactions and washed with deionized water and dried at 105° C. in oven for one hour. After drying the catalyst and performing catalyst characterization using BET/BJH analysis, the recovered catalyst was reused in the same reaction condition as the fresh catalyst was used. FIG. 14 shows that the same itaconic acid conversion was achieved with both fresh and reused hydrotalcite. FIG. 14 also shows that methacrylic acid yield increased (1.65 factor increase in yield) and is higher in the reused hydrotalcite run. Further catalyst characterization is required in order to determine the reason for increasing activity of hydrotalcite after it is reacted. Similar results were obtained using citric acid (FIG. 14, a 2.55 factor increase in MA yield when the catalyst was recovered and reused).

Surface area, total pore volume and average pore size of hydrotalcite was measured with BET and BJH analysis (Table 4). Surface area is determined using nitrogen adsorption in a Quantachrome Austosorb-1C with BET analysis. Total pore volume and average pore size are determined using nitrogen desorption curves with BJH analysis. The surface area, average pore size and total pore volume of the reacted hydrotalcite decreased after the first reaction as expected. Interestingly, the catalyst characterization for the reused hydrotalcite indicates an increase in surface area and total pore volume. The increased surface area and pore volume of reused hydrotalcite might be attributed to the removal of interlayer water molecules and carbon dioxide from the carbonate anion present in the brucite layer (Onda et al., 2008).

Example 7: Effect of Substrate Concentration on Methacrylic Acid Yield

Figure 15:
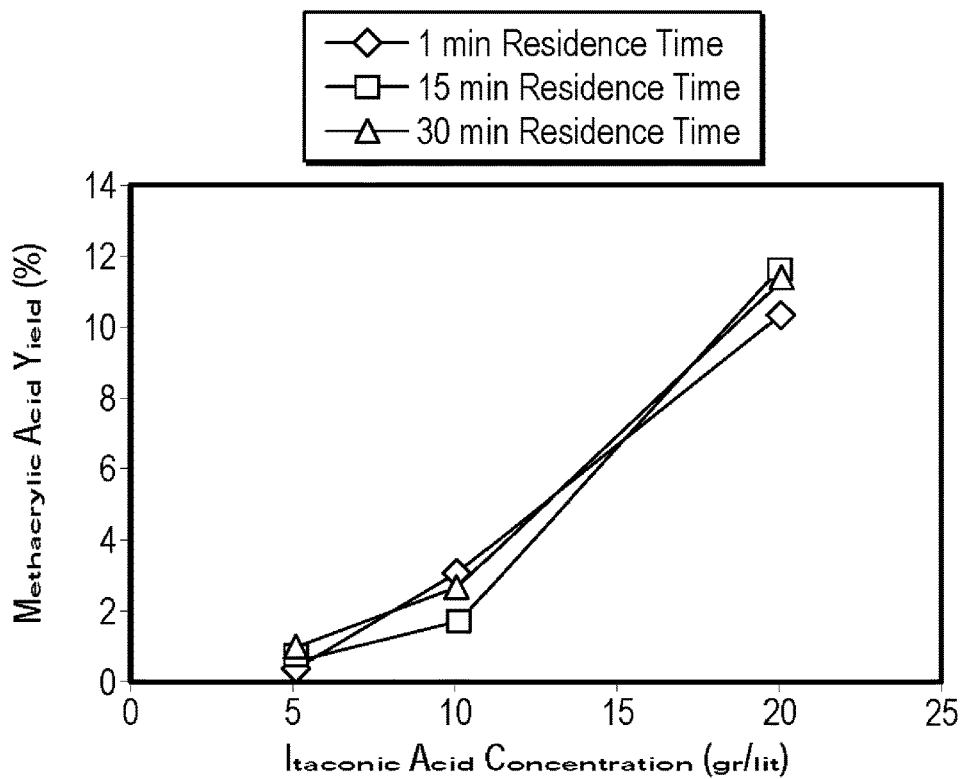
FIG. 15 is a graph showing the effect of itaconic acid concentration on MAA yield (1 g hydrotalcite-250° C.)
Figure 16:
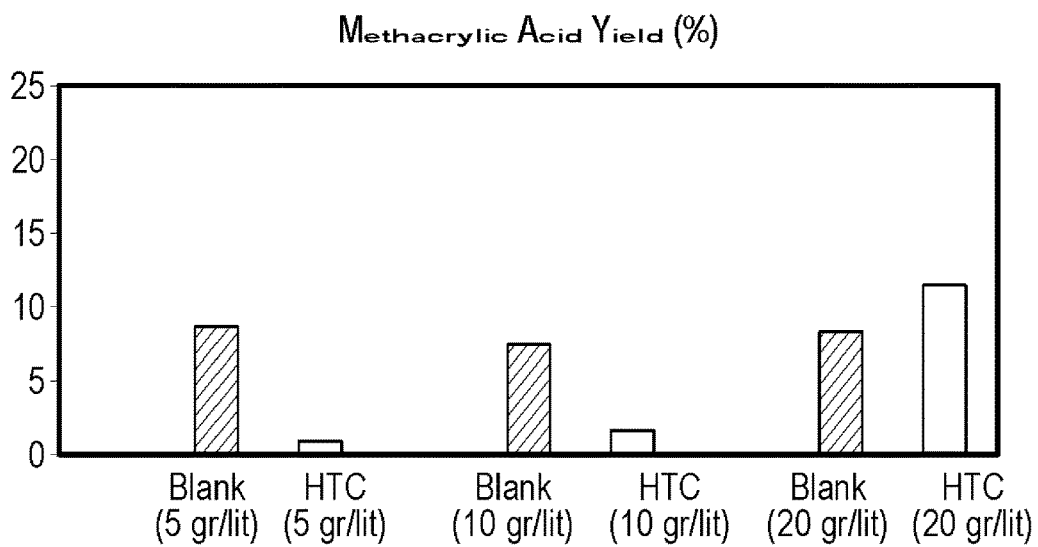
FIG. 16 is a graph showing the effect of adding HTC on lower concentrations of itaconic acid (1 g hydrotalcite-250° C.-15 minutes residence time)

In order to study the effect of itaconic acid concentration on methacrylic acid yield, a series of experiments with varying substrate concentration were performed at 250° C. with 1 gram hydrotalcite. In all three residence times, the highest methacrylic acid was achieved in 20 g/lit itaconic acid concentrations (FIG. 15) and methacrylic acid yield did not show a remarkable increase or decrease with increasing residence time in each concentration. The 1 minute residence time experiments on both citric acid and itaconic acid show promising results for production of methacrylic acid continuously. Blank runs were also performed on 5, 10, 20 g/lit concentrations of itaconic acid. At 5 and 10 g/lit itaconic acid concentration, methacrylic acid yield was higher in blank runs in comparison to runs with one gram hydrotalcite which means that hydrotalcite has an inhibition effect on the decarboxylation reaction in lower concentrations of itaconic acid (FIG. 16).

Example 8: Production of Methacrylic Acid in Continuous Packed Bed Reactor System Preliminary results from studying the effect of itaconic acid residence time on methacrylic acid yield in presence of hydrotalcite verify that methacrylic acid yield rises rapidly to almost a steady state value. The methacrylic acid yield value in shorter residence times is approximately equal to the methacrylic acid yield value in longer residence times. These promising results lead us to design a process in order to produce methacrylic acid continuously using solid base catalysts. With this purpose, decarboxylation reactions will be performed in a continuous packed bed reactor system (Parr Instrument Company). The catalysts are loaded into the stainless steel tube reactor with inner diameter of 2.4 cm and length of 38 cm. Since our best results occur at 250° C. in the batch reactor system, this temperature will be used as the operating temperature in the continuous packed bed reactor system. In order to keep the substrate (carboxylic acid in water solution) in liquid phase during the reaction, the starting reaction pressure will be higher than the vapor pressure of water at 250° C. (600 psig). The $$\frac{\text{Concentration of Substrate}}{\text{Mass of Catalyst}}$$

ratio for the best results in the batch reactor system will help us design the process in the continuous reactor system. Residence time in packed bed reactors is equal to volume of bed/flow rate. Therefore measuring the bulk density of the catalyst and knowing the optimized mass of catalyst, we will be able to calculate the volume of catalyst bed. Therefore, with changing flowrate, liquid residence time will change. 50 grams of liquid feedstock will be used for each reaction, resulting in a total reaction time 100 minutes. Nitrogen is used as a carrier gas to the reactor at a rate of 100 mL/min.

Example 9: Production of Methacrylic Acid from 2-Hydroxyisobutyric Acid (HIB or HIBA)

Figure 17A:
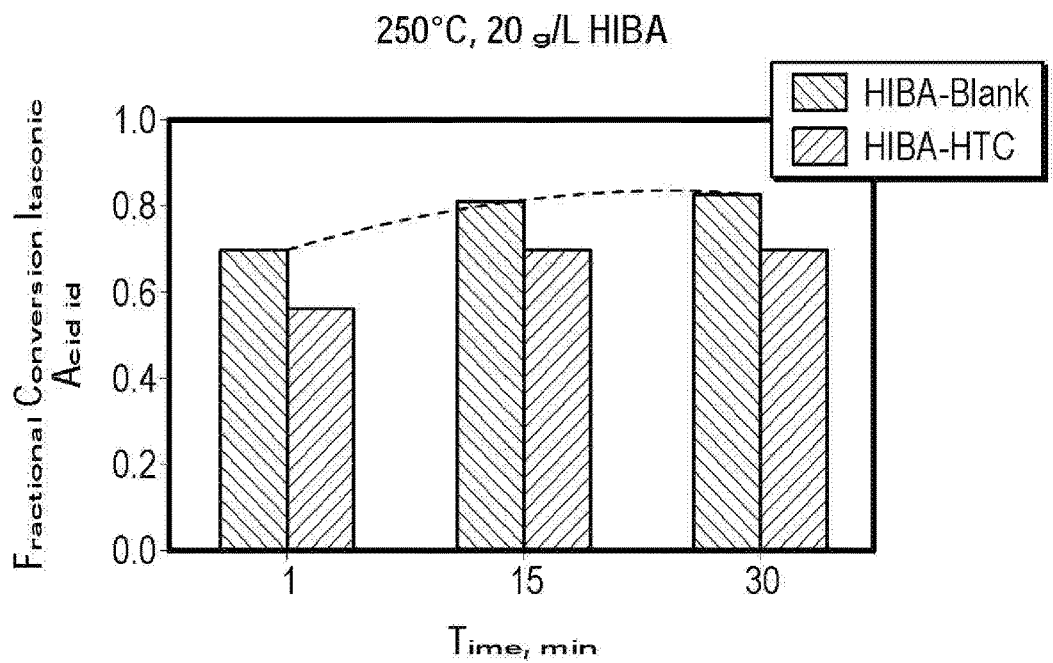
FIG. 17A and FIG. 17B are graphs showing the conversion of 2-hydroxyisobutryic acid to methacrylic acid using subcritical water at 250° C. wherein HIBA is 2-Hydroxyisobutyric acid and HTC is hydrotalcite.
Figure 17B:
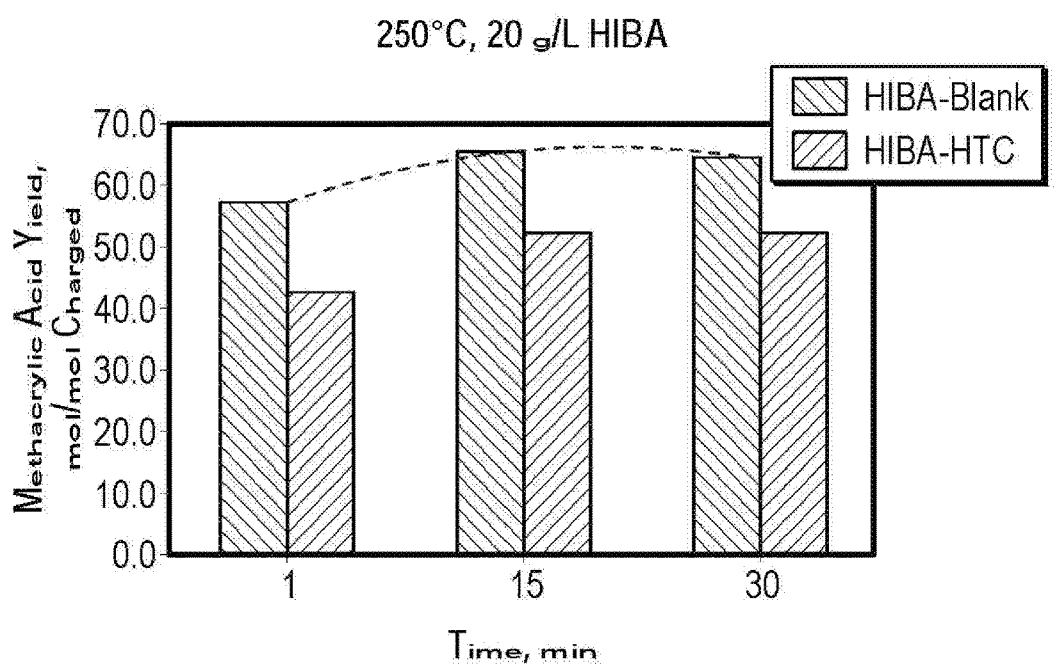

As described supra, 2-hydroxyisobutyric acid was reacted in subcritical water at 250° C. for different residence times. The reactions were performed in subcritical water alone and in the presence of hydrotalcite. 2-Hydroxyisobutyric acid (HIBA) can be produced via fermentation using genetically engineered microbial strains. As noted in FIG. 17, HIBA conversion approaches 80% in 15 minutes and achieves 66% yield, using subcritical water at 250° C. Since subcritical water can act as an acid under these conditions we theorize that an acid catalyzed reaction is occurring under these conditions leading to dehydration of HIBA to form methacrylic acid.

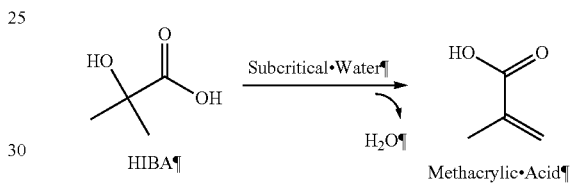

The results of preliminary studies using hydrotalcite indicate that using this solid base catalyst increases the methacrylic acid yield in decarboxylation reaction of itaconic acid and citric acid. High methacrylic acid yields in low residence times lead us to design a process in order to produce methacrylic acid continuously (in packed bed reactor system). Literature review analysis indicates the use of transition-metal catalysts such as palladium and platinum in production of methacrylic acid from itaconic acid and citric acid. However, we were not able to reach high methacrylic acid yields with Pd/C catalyst. We expect that synthesizing a solid base catalyst with acid sites and impregnated with a transition metal catalyst will be effective on increasing the methacrylic acid yield in decarboxylation reaction of carboxylic acids. Our results clearly indicate that there is an optimum substrate concentration to catalyst mass ratio in decarboxylation of citric acid and itaconic acid to methacrylic acid. Therefore we expect the same trend for decarboxylation of citramalic acid to methacrylic acid in presence of solid base catalysts. The reacted hydrotalcite showed higher activity in comparison to the fresh hydrotalcite. These promising results about the reusability of catalyst also confirm that this solid base catalyst can be a proper substitute for homogeneous base catalysts which are difficult to recycle and separation.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art.

It will be appreciated by persons skilled in the art that the present invention is not limited by what has been particularly shown and described herein above.

LITERATURE CITED

Ai M., Fujihashi H., Hosoi S., Yoshida A. (2003) Production of methacrylic acid by vapor-phase aldol condensation of propionic acid with formaldehyde over silica-supported metal phosphate catalysts. Applied catalysis A: general 252:185-191.

Albers P., Pietsch J., Parker S. F. (2001) Poisoning and deactivation of palladium catalysts. Journal of Molecular Catalysis A: Chemical 173:275-286.

An J., Bagnell L., Cablewski T., Strauss C. R., Trainor R. W. (1997) Applications of high-temperature aqueous media for synthetic organic reactions. The Journal of organic chemistry 62:2505-2511.

Bauer, W. Methacrylic Acid and derivatives. Ullmans Encyclopedia of industrial chemistry, 5th ed.; Elvers, B., Hawkins, S., Schulz, G., Eds; VCH; Weinheim, F R G, 1990; Vol. A16:441-452.

Beck D. D., Sommers J. W. (1995) Impact of sulfur on the performance of vehicle-aged palladium monoliths. Applied Catalysis B: Environmental 6:185-200.

Bruce, W. F. Aconitic Acid. Organic Synthesis Collective; Blatt, A. H., Ed; J. Wiley & Sons: New York, 1943; Vol. 2:12-14

Carlsson M., Habenicht C., Kam L. C., Antal M. J. J., Bian N., Cunningham R. J., Jones M. J. (1994) Study of the sequential conversion of citric to itaconic to methacrylic acid in near-critical and supercritical water. Industrial & engineering chemistry research 33:1989-1996.

Fu J., Shi F., Thompson Jr L., Lu X., Savage P. E. (2011) Activated carbons for hydrothermal decarboxylation of fatty acids. ACS Catalysis 1:227-231.

Hattori H. (2014) Solid base catalysts: fundamentals and their applications in organic reactions. Applied Catalysis A: General.

Johnson W. (1979) Comprehensive organic chemistry the synthesis and reactions of organic compounds: Volume 5 (Biological compounds; edited by E. Haslam, Sheffield), Pergamon.

Kuenz A., Gallenmüller Y., Willke T., Vorlop K.-D. (2012) Microbial production of itaconic acid: developing a stable platform for high product concentrations. Applied microbiology and biotechnology 96:1209-1216.

Kus N. S. (2012) Organic reactions in subcritical and supercritical water. Tetrahedron 68:949-958.

L'Argentière P., Liprandi D., Cagnola E., Fígoli N. (1997) [PdCl$_2$ (NH$_2$(CH$_2$)$_{12}$CH$_3$)$_2$] supported on γ-Al$_2$O$_3$ as catalyst for selective hydrogenation. Catalysis letters 44:101-107.

Le Nôtre J., Witte-van Dijk S., van Haveren J., Scott E. L., Sanders J. P. (2014) Synthesis of Bio-Based Methacrylic Acid by Decarboxylation of Itaconic Acid and Citric Acid Catalyzed by Solid Transition-Metal Catalysts. ChemSusChem 7:2712-2720.

Li J., Brill T. B. (2001) Spectroscopy of Hydrothermal Reactions 16: Kinetics of Decarboxylation/Hydrolysis of Methyl Propiolate Ester and Decarboxylation of Propiolic Acid at 150-210° C. and 275 Bar. The Journal of Physical Chemistry A 105:6171-6175.

Matsubara S., Yokota Y., Oshima K. (2004) Palladium-catalyzed decarboxylation and decarbonylation under hydrothermal conditions: decarboxylative deuteration. Organic letters 6:2071-2073.

Na J.-G., Yi B. E., Kim J. N., Yi K. B., Park S.-Y., Park J.-H., Kim J.-N., Ko C. H. (2010) Hydrocarbon production from decarboxylation of fatty acid without hydrogen. Catalysis Today 156:44-48.

Nagasawa T., Nakamura T., Yamada H. (1990) ε-Caprolactam, a new powerful inducer for the formation of *Rhodococcus rhodochrous* J1 nitrilase. Archives of microbiology 155:13-17.

Nikolopoulos A., Jang B.-L., Spivey J. (2005) Acetone condensation and selective hydrogenation to MIBK on Pd and Pt hydrotalcite-derived Mg Al mixed oxide catalysts. Applied Catalysis A: General 296:128-136.

Onda A., Ochi T., Kajiyoshi K., Yanagisawa K. (2008) Lactic acid production from glucose over activated hydrotalcites as solid base catalysts in water. Catalysis Communications 9:1050-1053.

Pyo S.-H., Dishisha T., Dayankac S., Gerelsaikhan J., Lundmark S., Rehnberg N., Hatti-Kaul R. (2012) A new route for the synthesis of methacrylic acid from 2-methyl-1,3-propanediol by integrating biotransformation and catalytic dehydration. Green Chemistry 14:1942-1948.

Spivey J. J., Gogate M. R., Zoeller J. R., Colberg R. D. (1997) Novel catalysts for the environmentally friendly synthesis of methyl methacrylate. Industrial & engineering chemistry research 36:4600-4608.

Steiger M. G., Blumhoff M. L., Mattanovich D., Sauer M. (2013) Biochemistry of microbial itaconic acid production. Frontiers in microbiology 4.

Tai J., Davis R. J. (2007) Synthesis of methacrylic acid by aldol condensation of propionic acid with formaldehyde over acid-base bifunctional catalysts. Catalysis today 123:42-49.

White R. J., Luque R., Budarin V. L., Clark J. H., Macquarrie D. J. (2009) Supported metal nanoparticles on porous materials. Methods and applications. Chemical Society Reviews 38:481-494.

Willke T., Vorlop K.-D. (2001) Biotechnological production of itaconic acid. Applied microbiology and biotechnology 56:289-295.

Xu C., Teja A. S. (2006) Supercritical water synthesis and deposition of iron oxide (α-Fe$_2$O$_3$) nanoparticles in activated carbon. The Journal of supercritical fluids 39:135-141.

The invention claimed is:

1. A method of producing methacrylic acid comprising reacting a substrate with a palladium nitrate catalyst comprising a hydrotalcite under conditions sufficient to produce methacrylic acid in a single step, wherein the substrate is selected from the group consisting of 2-hydroxyisobutyric acid or salts thereof, itaconic acid or salts thereof, citric acid or salts thereof, citramalic acid or salts thereof, and combinations thereof.

2. The method of claim 1, wherein the hydrotalcite is a solid form of hydrotalcite.

3. The method of claim 2, wherein the solid form of hydrotalcite is porous.

4. The method of claim 1, further comprising reacting in the presence of an inert gas.

5. The method of claim 1, further comprising reacting in the presence of subcritical water or supercritical water.

6. The method of claim 1, wherein a temperature of reacting is from about ambient temperature to about 700° C.

7. The method of claim 1, wherein a pressure of reacting is from about ambient pressure to about 1000 pounds per square inch.

8. The method according to claim 1, wherein a residence time of the reacting is from about 0.5 minutes to about 60 minutes.

9. The method of claim 1, wherein a catalyst turnover number is from about 10 to about $10^6$.

10. The method of claim 1, wherein a temperature of the reacting is from about 200° C. to about 250° C.; and a pressure of the reacting is about 500 pounds per square inch, and the reacting takes place in the presence of helium; and from about 1 to about 30 minutes,
wherein the substrate is at a concentration of from about 5 to about 20 grams per liter;
and wherein the catalyst weight is from about 0.125 g to about 2 grams.

11. A method of producing methacrylic acid comprising reacting a substrate with a catalyst comprising a hydrotalcite under conditions sufficient to produce methacrylic acid in a single step, wherein the substrate is selected from the group consisting of 2-hydroxyisobutyric acid or salts thereof, itaconic acid or salts thereof, citric acid or salts thereof, citramalic acid or salts thereof, and combinations thereof, and wherein the hydrotalcite is both solid and porous.

12. The method of claim 11, further comprising reacting in the presence of subcritical water or supercritical water.

13. The method of claim 11, wherein the catalyst comprises a transition metal or a salt thereof, wherein the transition metal is selected from the group consisting of palladium, platinum, and rhodium.

14. The method of claim 11, wherein a catalyst turnover number is from about 10 to about $10^6$.

15. A method of producing methacrylic acid comprising reacting a substrate with a catalyst comprising a hydrotalcite under conditions sufficient to produce methacrylic acid in a single step;
wherein the substrate is selected from the group consisting of 2-hydroxyisobutyric acid or salts thereof, itaconic acid or salts thereof, citric acid or salts thereof, citramalic acid or salts thereof, and combinations thereof; and
further comprising reacting in the presence of subcritical water or supercritical water.

16. The method of claim 15, wherein the catalyst comprises a transition metal or a salt thereof, wherein the transition metal is selected from the group consisting of palladium, platinum, and rhodium.

17. The method of claim 15, wherein the hydrotalcite is a solid form of hydrotalcite, wherein the solid form of hydrotalcite is porous.

18. The method of claim 15, wherein a catalyst turnover number is from about 10 to about $10^6$.

19. A method of producing methacrylic acid comprising reacting a substrate with a catalyst comprising a hydrotalcite under conditions sufficient to produce methacrylic acid in a single step;
wherein the substrate is selected from the group consisting of 2-hydroxyisobutyric acid or salts thereof, itaconic acid or salts thereof, citric acid or salts thereof, citramalic acid or salts thereof, and combinations thereof; and
wherein a catalyst turnover number is from about 10 to about $10^6$.

20. The method of claim 19, wherein the catalyst comprises a transition metal or a salt thereof, wherein the transition metal is selected from the group consisting of palladium, platinum, and rhodium.

21. The method of claim 19, further comprising reacting in the presence of subcritical water or supercritical water.

22. The method of claim 19, wherein the hydrotalcite is a solid form of hydrotalcite, wherein the solid form of hydrotalcite is porous.

* * * * *